(12) United States Patent
Boveja et al.

(10) Patent No.: US 7,062,330 B1
(45) Date of Patent: *Jun. 13, 2006

(54) ELECTRICAL STIMULATION ADJUNCT (ADD-ON) THERAPY FOR URINARY INCONTINENCE AND UROLOGICAL DISORDERS USING IMPLANTED LEAD STIMULUS-RECEIVER AND AN EXTERNAL PULSE GENERATOR

(76) Inventors: Birinder R. Boveja, P.O. Box 210095, Milwaukee, WI (US) 53221; Angely Widhany, P.O. Box 210095, Milwaukee, WI (US) 53221

(*) Notice: Subject to any disclaimer, the term of this patent is extended or adjusted under 35 U.S.C. 154(b) by 659 days.

This patent is subject to a terminal disclaimer.

(21) Appl. No.: 10/195,961

(22) Filed: Jul. 16, 2002

Related U.S. Application Data

(63) Continuation-in-part of application No. 09/752,083, filed on Dec. 29, 2000, now Pat. No. 6,505,074, which is a continuation-in-part of application No. 09/178,060, filed on Oct. 26, 1998, now Pat. No. 6,205,359.

(51) Int. Cl.
    *A61N 1/08* (2006.01)
(52) U.S. Cl. ...................................... 607/41
(58) Field of Classification Search ............ 607/39–41, 607/118, 133, 138
See application file for complete search history.

(56) References Cited

U.S. PATENT DOCUMENTS

| 3,796,221 A | 3/1974 | Hagfors et al. ............. 128/421 |
| 3,870,051 A * | 3/1975 | Brindley ...................... 607/40 |
| 4,771,779 A | 9/1988 | Tanagho et al. |
| 5,193,539 A | 3/1993 | Schulman et al. ............ 607/61 |
| 5,304,206 A | 4/1994 | Baker, Jr. et al. |
| 5,405,367 A | 4/1995 | Schulman et al. ............ 607/61 |
| 6,055,456 A | 4/2000 | Gerber |
| 6,735,474 B1 * | 5/2004 | Loeb et al. .................... 607/41 |

* cited by examiner

Primary Examiner—Jeffrey R. Jastrzab

(57) ABSTRACT

A method and system for neuromodulation therapy for urinary incontinence and urological disorders comprises an implantable lead stimulus-receiver, and an external stimulator-transmitter having a power source, controlling circuitry, and predetermined programs. The stimulator-transmitter further includes a primary coil which inductively transfers electrical signals to the lead-receiver, which is also in electric contact with the sacral nerves. The external stimulator-transmitter emits electrical pulses to stimulate the sacral plexus according to a predetermined program. In one mode of operation, the operator may program one of the predetermined programs, in another mode, the electrical parameters may be "custom" programmed for the patient, and stored in the memory.

34 Claims, 21 Drawing Sheets

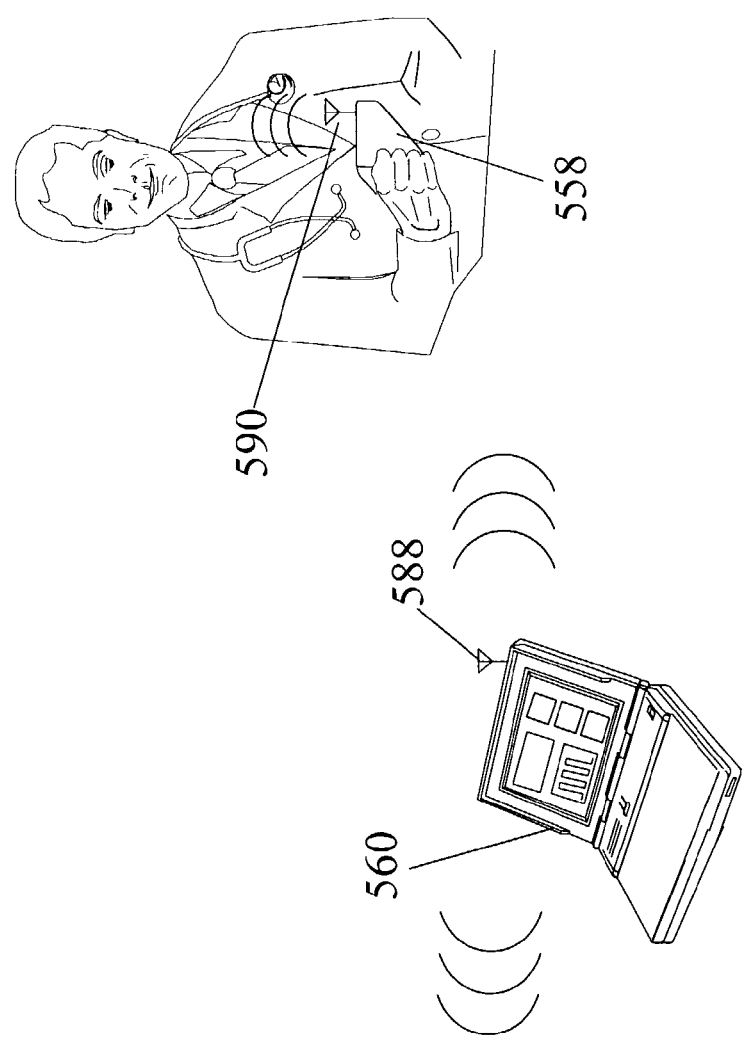
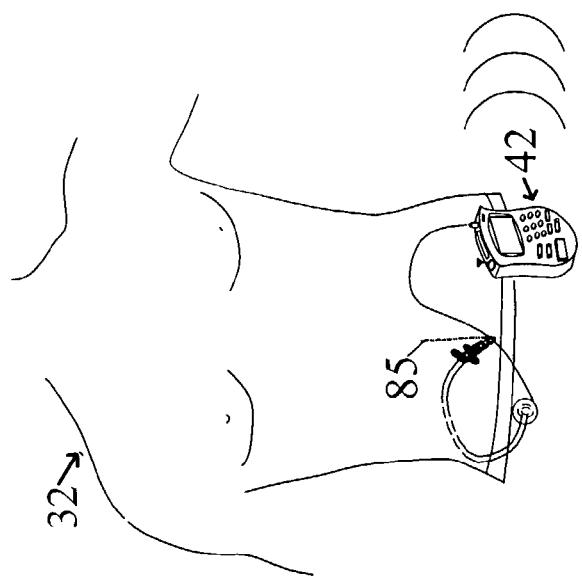
FIG. 20

ELECTRICAL STIMULATION ADJUNCT (ADD-ON) THERAPY FOR URINARY INCONTINENCE AND UROLOGICAL DISORDERS USING IMPLANTED LEAD STIMULUS-RECEIVER AND AN EXTERNAL PULSE GENERATOR

This is a Continuation-in-Part of application Ser. No. 09/752,083 filed Dec. 29, 2000, now U.S. Pat. No. 6,505, 074, which is a Continuation-in Part of application Ser. No. 09/178,060 now U.S. Pat. No. 6,205,359 filed Oct. 26, 1998. Priority is claimed from these applications, and the prior applications being incorporated herein by reference.

FIELD OF THE INVENTION

The present invention relates to electrical neuromodulation therapy for medical disorders, more specifically neuromodulation therapy for urinary incontinence and urological disorders utilizing an implanted lead stimulus-receiver and an external pulse generator-transmitter.

BACKGROUND OF THE INVENTION

Biological and human clinical research has shown utility of electrical nerve stimulation for urinary incontinence and a broad group of urological disorders. This invention is directed to the adjunct therapy for these disorders utilizing an implanted lead-receiver and an external stimulator with predetermined stimulation programs.

In considering the background of urinary urge incontinence, FIG. 1 shows a sagittal section of the human female pelvis showing the bladder 10 and urethra 13 in relation to other anatomic structures. Urinary continence requires a relaxed bladder during the collecting phase and permanent closure of the urethra, whereas at micturition (urination), an intravesical pressure above the opening pressure of the simultaneously relaxing urethra has to be generated. These functions of the bladder and urethra are centrally coordinated and non-separable. At bladder filling, the sensation of urge is mediated by slowly adapting mechanoreceptors in the bladder wall and the same receptors provide the triggering signal for micturition and the main driving force for a sustained micturition contraction. The mechanoreceptors are, technically speaking, tension receptors. It has been found that they respond equally well to tension increases induced passively by bladder filling and those induced actively by a detrusor contraction. These receptors have high dynamic sensitivity and are easily activated by external pressure transients, as may occur during coughing or tapping of the abdominal wall. Their faithful response to active changes in bladder pressure is well illustrated.

When sufficiently activated, the mechanorecptors trigger a coordinated micturition reflex via a center in the upper pons 88, as depicted schematically in FIG. 2. The reflex detrusor 92 (muscle in the wall of the urinary bladder) contraction generates an increased bladder pressure and an even stronger activation of the mechanoreceptors. Their activity in turn reinforces the pelvic motor output to the bladder, which leads to a further increase in pressure and more receptor activation and so on. In this way, the detrusor contraction is to a large extent self generating once initiated. Such a control mechanism usually is referred to as a positive feedback, and it may explain the typical all-or-nothing behavior of the parasympathetic motor output to the bladder. Once urine enters the urethra, the contraction is further enhanced by reflex excitation from urethral receptors. Quantitatively, the bladder receptors are most important.

A great advantage of the positive feedback system is that it ascertains a complete emptying of the bladder during micturition. As long as there is any fluid left in the lumen, the intravesical pressure will be maintained above the threshold for the mechanoreceptors and thus provide a continuous driving force for the detrusor. A drawback with this system is that it can easily become unstable. Any stimulus that elicits a small burst of impulses in mechanoreceptor afferents may trigger a full-blown micturition reflex. To prevent this from happening during the filling phase, the neuronal system controlling the bladder is equipped with several safety devices both at the spinal and supraspinal levels.

The best-known spinal mechanism is the reflex control of the striated urethral sphincter 90, which increases its activity in response to bladder mechanoreceptor activation during filling. An analogous mechanism is Edvardsen's reflex, which involves machanoreceptor activation of inhibitory sympathetic neurons to the bladder. The sympathetic efferents have a dual inhibitory effect, acting both at the postganglionic neurons in the vesical ganglia and directly on the detrusor muscle of the bladder 92. The sphincter and sympathetic reflexes are automatically turned off at the spinal cord level during a normal micturition. At the supraspinal level, there are inhibitory connections from the cerebral cortex and hypothalamus to the pontine micturition center. The pathways are involved in the voluntary control of continence. Other inhibitory systems seem to originate from the pontine and medullary parts of the brainstem with at least partly descending connections.

Bladder over-activity and urinary urge incontinence may result from an imbalance between the excitatory positive feedback system of the bladder 10 and inhibitory control systems causing a hyperexcitable voiding reflex. Such an imbalance may occur after macroscopic lesions at many sites in the nervous system or after minor functional disturbances of the excitatory or inhibitory circuits. Urge incontinence due to detrusor instability seldom disappears spontaneoulsly. The symptomatic pattern also usually is consistent over long periods.

Based on clinical experience, subtypes of urinary incontinence include, Phasic detrusor instability and uninhibited overactive bladder. Phasic detrusor instability is characterized by normal or increased bladder sensation, phasic bladder contractions occurring spontaneously during bladder filling or on provocation, such as by rapid filling, coughing, or jumping. This condition results from a minor imbalance between the bladder's positive-feedback system and the spinal inhibitory mechanisms. Uninhibited overactive bladder is characterized by loss of voluntary control of micturition and impairment of bladder sensation. The first sensation of filling is experienced at a normal or lowered volume and is almost immediately followed by involuntary micturition. The patient does not experience a desire to void until she/he is already voiding with a sustained detrusor contraction and a concomitant relaxation of the urethra, i.e., a well-coordinated micturition reflex. At this stage, she/he is unable to interrupt micturition voluntarily. The sensory disturbance of these subjects is not in the periphery, at the level of bladder mechanoreceptors, as the micturition reflex occurs at normal or even small bladder volumes. More likely, the suprapontine sensory projection to the cortex is affected. Such a site is consistent with the coordinated micturition and the lack of voluntary control. The uninhibited overactive bladder is present in neurogenic dysfunction.

Since bladder over-activity results from defective central inhibition, it seems logical to improve the situation by reinforcing some other inhibitory system. Patients with stress and urge incontinence are difficult to treat adequately. Successful therapy of the urge component does not influence the stress incontinence. While an operation for stress incontinence sometimes results in deterioration of urgency. Electro stimulation is a logical alternative in mixed stress and urge incontinence, since the method improves urethral closure as well as bladder control. Drug treatment often is insufficient and, even when effective, does not lead to restoration of a normal micturition pattern.

Neuromodulation is a technique that applies electrical stimulation to the sacral nerves, (a general diagram of spinal cord and sacral nerves 85 is shown in FIG. 3). The aim of this treatment modality is to achieve detrusor 92 inhibition by chronic electrical stimulation of afferent somatic sacral nerve fibers 85 via implanted electrodes coupled to a subcutaneously placed pulse generation means.

The rationale of this treatment modality is based on the existence of spinal inhibitory systems that are capable of interrupting a detrusor 92 contraction. Inhibition can be achieved by electrical stimulation of afferent anorectal branches of the pelvic nerve, afferent sensory fibers in the pudendal nerve and muscle afferents from the limbs. Most of these branches and fibers reach the spinal cord via the dorsal roots of the sacral nerves 85. Of the sacral nerve roots the S3 root is the most practical for use in chronic electrical stimulation.

Most nerves in the human body are composed of thousands of fibers, of different sizes designated by groups A, B and C, which carry signals to and from the brain. A peripheral nerve, for example, may have approximately 100,000 fibers of the three different types, each carrying signals. Each axon or fiber of that nerve conducts only in one direction, in normal circumstances. The A and B fibers are myelinated (i.e., have a myelin sheath, constituting a substance largely composed of fat, whereas the C fibers are unmyelinated.

A commonly used nomenclature for peripheral nerve fibers, using Roman and Greek letters, is given in the table below:

| Group | External Diameter (μm) | Conduction Velocity (m/sec) |
|---|---|---|
| Myelinated Fibers | | |
| Aα or IA | 12–20 | 70–120 |
| Aβ: | | |
| IB | 10–15 | 60–80 |
| II | 5–15 | 30–80 |
| Aγ | 3–8 | 15–40 |
| Aδ or III | 3–8 | 10–30 |
| B | 1–3 | 5–15 |
| Unmyelinted fibers | | |
| C or IV | 0.2–1.5 | 0.5–2.5 |

The diameters of group A and group B fibers include the thickness of the myelin sheaths. Group A is further subdivided into alpha, beta, gamma, and delta fibers in decreasing order of size. There is some overlapping of the diameters of the A, B, and C groups because physiological properties, especially the form of the action potential, are taken into consideration when defining the groups. The smallest fibers (group C) are unmyelinated and have the slowest conduction rate, whereas the myelinated fibers of group B and group A exhibit rates of conduction that progressively increase with diameter. Group B fibers are not present in the nerves of the limbs; they occur in white rami and some cranial nerves.

Compared to unmyelinated fibers, myelinated fibers are typically larger, conduct faster, have very low stimulation thresholds, and exhibit a particular strength-duration curve or respond to a specific pulse width versus amplitude for stimulation. The A and B fibers can be stimulated with relatively narrow pulse widths, from 50 to 200 microseconds (μs), for example. The A fiber conducts slightly faster than the B fiber and has a slightly lower threshold. The C fibers are very small, conduct electrical signals very slowly, and have high stimulation thresholds typically requiring a wider pulse width (300–1,000 μs) and a higher amplitude for activation. Selective stimulation of only A and B fibers is readily accomplished. The requirement of a larger and wider pulse to stimulate the C fibers, however, makes selective stimulation of only C fibers, to the exclusion of the A and B fibers, virtually unachievable inasmuch as the large signal will tend to activate the A and B fibers to some extent as well.

In neuromodulation, the entire innervation system should be intact. As shown schematically in FIG. 5, the procedure consists of placing electrodes 61,62 in one of the sacral foraman as close to the pelvic plexus and pudendal nerve as possible and connecting the lead 59 with a means for electrical stimulation 49. The hypothesis behind neuromodulation of the sacral roots (sensory and motor) is to correct, by the use of regulating electrical impulses, the dys-synergic activities of the cholinergic, adrenergic, and motor reflex pathways that initiate vesical storage and micturition. Although some theories have been developed that explain the effects of neuromodulation, most of the results are based on empiric findings in human studies. Some animal experiments and electrophysiologic studies in humans show there is a spinal inhibitory action through the afferent branches of the pelvic and pudendal nerves. It is not clear whether neuromodulation primarily influences the micturiction center located near the thalamus in the brain. Some maintain that there is a direct correction of the dys-synergis of the pelvic floor (pudendal nerve) by influencing the abnormal contractility of the pelvic floor.

A neurophysiological explanation for the effectiveness of this treatment modality in detrusor instability is based on animal experiments and electrophysiological studies in humans. Electrical stimulation for the treatment of urinary incontinence has evolved over the past 40 years. The mechanism of action of electrical stimulation was investigated initially in animal models. Over 100 years ago, Griffiths demonstrated relaxation of a contracted detrusor during stimulation of the proximal pudendal nerve in the cat model and further work clarified the role of pudendal afferents in relation of the detrusor. Spinal inhibitory systems capable of interrupting a detrusor contraction can be activated by electrical stimulation of afferent anorectal branhes of the pelvic nerve, afferent sensory fibers in the pudendal nerve and muscle afferents from the limbs. The effectiveness of neuromodulation in humans has been objectively demonstrated by urodynamic improvement, especially in light of the fact that such effects have not been noted in drug trials.

Neuromodulation also acts on neural reflexes but does so internally by stimulation of the sacral nerves 85. Sacral nerve 85 stimulation is based on research dedicated to the understanding of the voiding reflex as well as the role and influence of the sacral nerves 85 on voiding behavior. This research led to the development of a technique to modulate dysfunctional voiding behavior through sacral nerve stimulation. It is thought that sacral nerve stimulation induces reflex mediated inhibitory effects on the detrusor through afferent and/or efferent stimulation of the sacral nerves 85.

Even though the precise mechanism of action of electrical stimulation in humans is not fully understood, it has been shown that sensory input traveling through the pudendal nerve can inhibit detrusor activity in humans. Most experts believe that non-implanted electrical stimulation works by stimulating the pudendal nerve afferents, with the efferent outflow causing contraction of the striated pelvic musculature. There is also inhibition of inappropriate detrusor activity, though the afferent mechanism has yet to be clarified. There is consensus that the striated musculature action is able to provide detrusor inhibiton in this setting, though data supporting this hypotheses are lacking.

In summary, the rationale for neuromodulation in the management of such patients is the observation that stimulation of the sacral nerves via electrical stimulation can inhibit inappropriate neural reflex behavior.

PRIOR ART

Prior art electrical neuromodulation for urinary incontinence, is generally directed to the use of an implantable lead and an implantable pulse generator technology or "cardiac pacemaker like" technology. In the prior art, the pulse generator is programmed via a "personnel computer (PC)" based programmer that is modified and adapted with a programmer wand which is placed on top of the skin over the pulse generator implant site. Each parameter is programmed independent of the other parameters. Therefore, millions of different combinations of programs are possible. In the current application, limited number of programs are pre-selected.

U.S. Pat. No. 4,771,779 (Tanagho et al) is directed to a system for controlling bladder evacuation, which consists of multiple implanted stimulation systems having electrodes positioned on nerves controlling external sphincter and bladder functions, and electronic control system which transmit to the stimulation systems. In this patent, by having multiple stimulation systems and means of controlling them, the interaction between stimulating the bladder and external sphincter can be controlled.

U.S. Pat. No. 6,055,456 (Gerber) is generally directed to an implantable medical lead for stimulation of sacral nerves. The lead containing a distal and a proximal electrode.

U.S. Pat. No. 3,796,221 (Hagfors) is directed to controlling the amplitude, duration and frequency of electrical stimulation applied from an externally located transmitter to an implanted receiver by inductively coupling. Electrical circuitry is schematically illustrated for compensating for the variability in the amplitude of the electrical signal available to the receiver because of the shifting of the relative positions of the transmitter-receiver pair. By highlighting the difficulty of delivering consistent pulses, this patent points away from applications such as the current invention, where consistent therapy needs to be continuously sustained over a prolonged period of time. The methodology disclosed is focused on circuitry within the receiver, which would not be sufficient when the transmitting coil and receiving coil assume significantly different orientation, which is likely in the current application. The present invention discloses a novel approach for this problem, utilizing a proximity sensor.

U.S. Pat. No. 5,304,206 (Baker, Jr. et al) is directed to activation techniques for implanted medical stimulators. The system uses either a magnet to activate the reed switch in the device, or tapping which acts through the piezoelectric sensor mounted on the case of the implanted device, or a combination of magnet and tapping sequence.

U.S. Pat. No. 5,193,539 (Schulman, et al) is generally directed to an addressable, implantable microstimulator that is of size and shape which is capable of being implanted by expulsion through a hypodermic needle. In the Schulman patent, up to 256 microstimulators may be implanted within a muscle and they can be used to stimulate in any order as each one is addressable, thereby providing therapy for muscle paralysis.

U.S. Pat. No. 5,405,367 (Schulman, et al) is generally directed to the structure and method of manufacture of an implantable microstimulator.

The advantage of the system and method as described in this application is that the patient is able, within limits, to select and alter a program for their comfort without going to the physician's office. Such a system is also cheaper for the patient, as it can be manufactured for a fraction of the cost of an implantable pulse generator. Additionally, since the implanted circuit does not have a battery implanted, this eliminates the need for surgical replacement as in an implantable pulse generator.

SUMMARY OF THE INVENTION

The present invention is directed to method and system for adjunct electrical neuromodulation therapy for urinary incontinence and neuro-urological disorders using predetermined programs with an external stimulator (transmitter). The system consists of an implantable lead stimulus-receiver containing circuitry, electrodes adapted for stimulation of sacral plexus, and a coil for coupling to the external transmitter. The external transmitter, which may be worn on a belt or carried in a pocket contains, electronic circuitry, power source, primary coil(s), and predetermined programs. The external stimulator (transmitter) emits modulated high frequency signals, which are received, processed, and delivered by the electrodes of the implanted lead stimulus receiver. The external primary coil and subcutaneous secondary coil are inductively coupled.

In one aspect of the invention the pulse generator contains a limited number of predetermined programs, which can be accessed directly without a programmer. The limited number of programs can be any number of programs even as many as 50 programs, and such a number is considered within the scope of this invention.

In another aspect of the invention, the electrical parameters can be "custom" programmed for the individual patient, and such customized parameters can be stored in memory.

In another feature of the invention, the system provides for proximity sensing means between the primary (external) and secondary (implanted) coils. Utilizing current technology, the physical size of the implantable lead-receiver has become relatively small. However, it is essential that the primary (external) and secondary (implanted) coils be positioned appropriately with respect to each other. The sensor technology incorporated in the present invention aids in the optimal placement of the external coil relative to a previously implanted subcutaneous coil. This is accomplished through a combination of external and implantable or internal components.

In another aspect of the invention, the implanted stimulus-receiver contains high value capacitors for storing charge.

Up to approximately 24 hours of stimulating power can be stored in these high-value capacitors.

In another aspect of the invention, the external pulse generator contains a telemetry module, whereby therapy can be controlled remotely.

Various other features, objects and advantages of the invention will be made apparent from the following description taken together with the drawings.

BRIEF DESCRIPTION OF THE DRAWINGS

For the purpose of illustrating the invention, there are shown in accompanying drawing forms which are presently preferred, it being understood that the invention is not intended to be limited to the precise arrangement and instrumentalities shown.

FIG. 20. is a schematic diagram showing wireless communication with the stimulus generator and a remote computer.

DETAILED DESCRIPTION OF THE INVENTION

The following description is of the current embodiment for carrying out the invention. This description is not to be taken in a limiting sense, but is made merely for the purpose of describing the general principles of the invention. The scope of the invention should be determined with reference to the claims.

The method and system for sacral nerve neuromodulation of this invention, comprises an implanted lead stimulus-receiver and an external transmitter. The external transmitter delivers predetermined modulated high frequency pulses which are converted to electrical pulses for modulating the sacral plexus, by the implanted lead-receiver stimulator. The external transmitter itself can be remotely controlled, and programmed. The implanted lead stimulus-receiver and external transmitter are coupled via wireless link.

Figure 1:
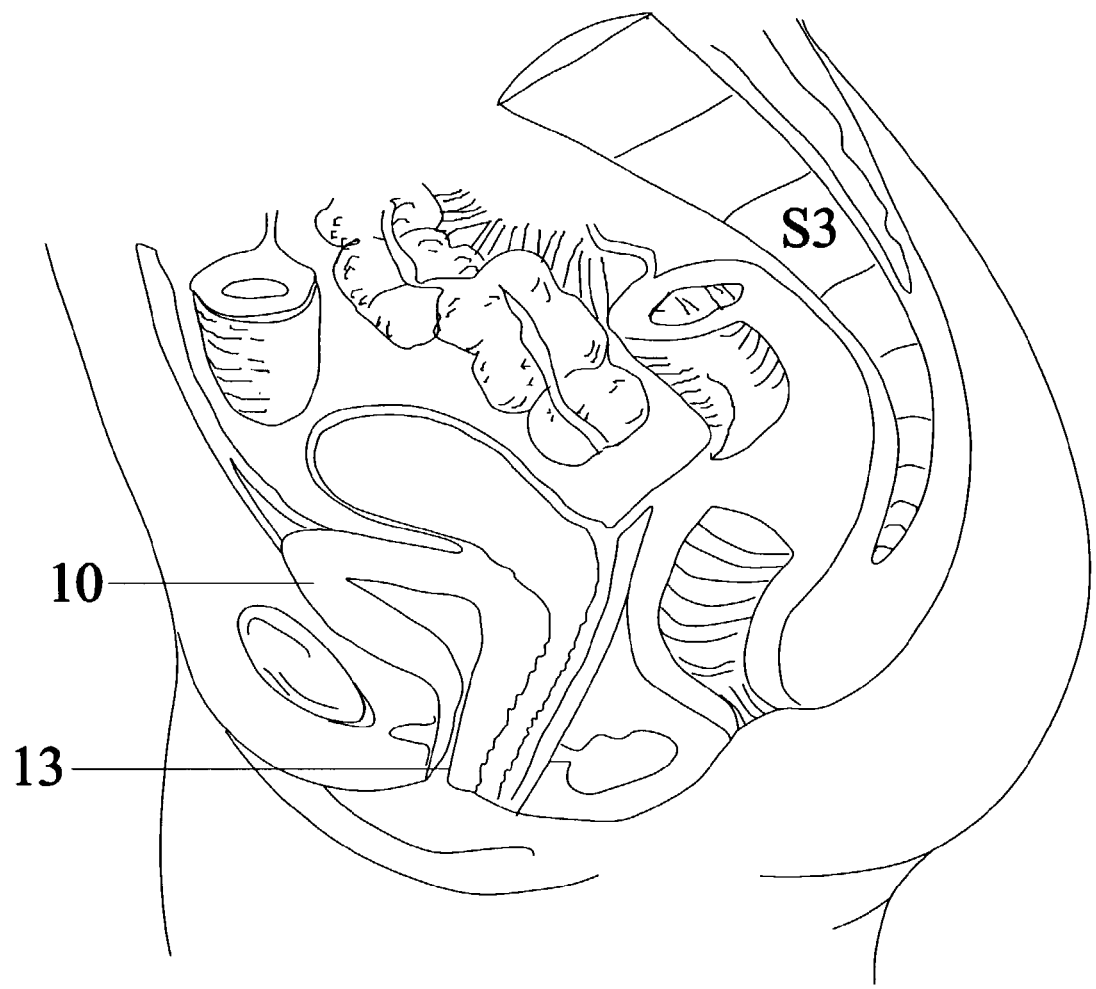
FIG. 1 shows a diagram of the sagittal section of the female pelvis, showing the relationship between various anatomic structures.
Figure 2:
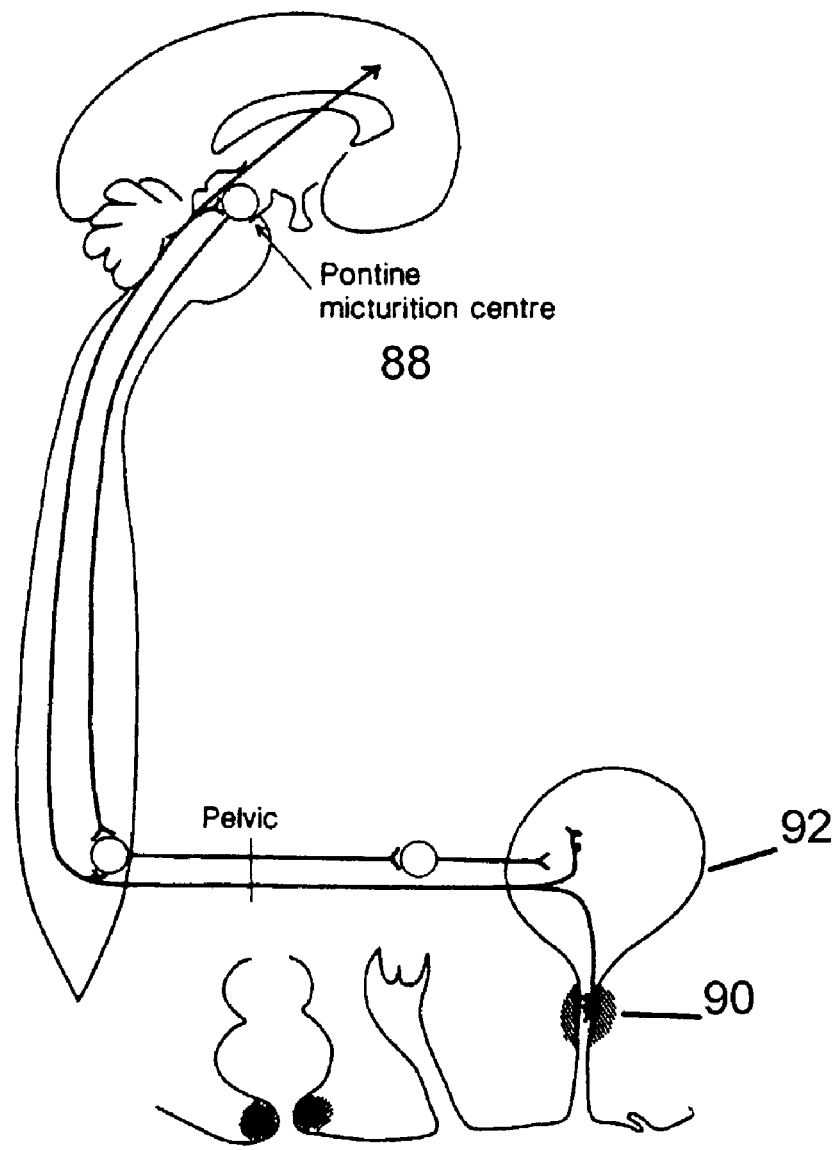
FIG. 2 is a schematic diagram showing physiological control of micturition.
Figure 3:
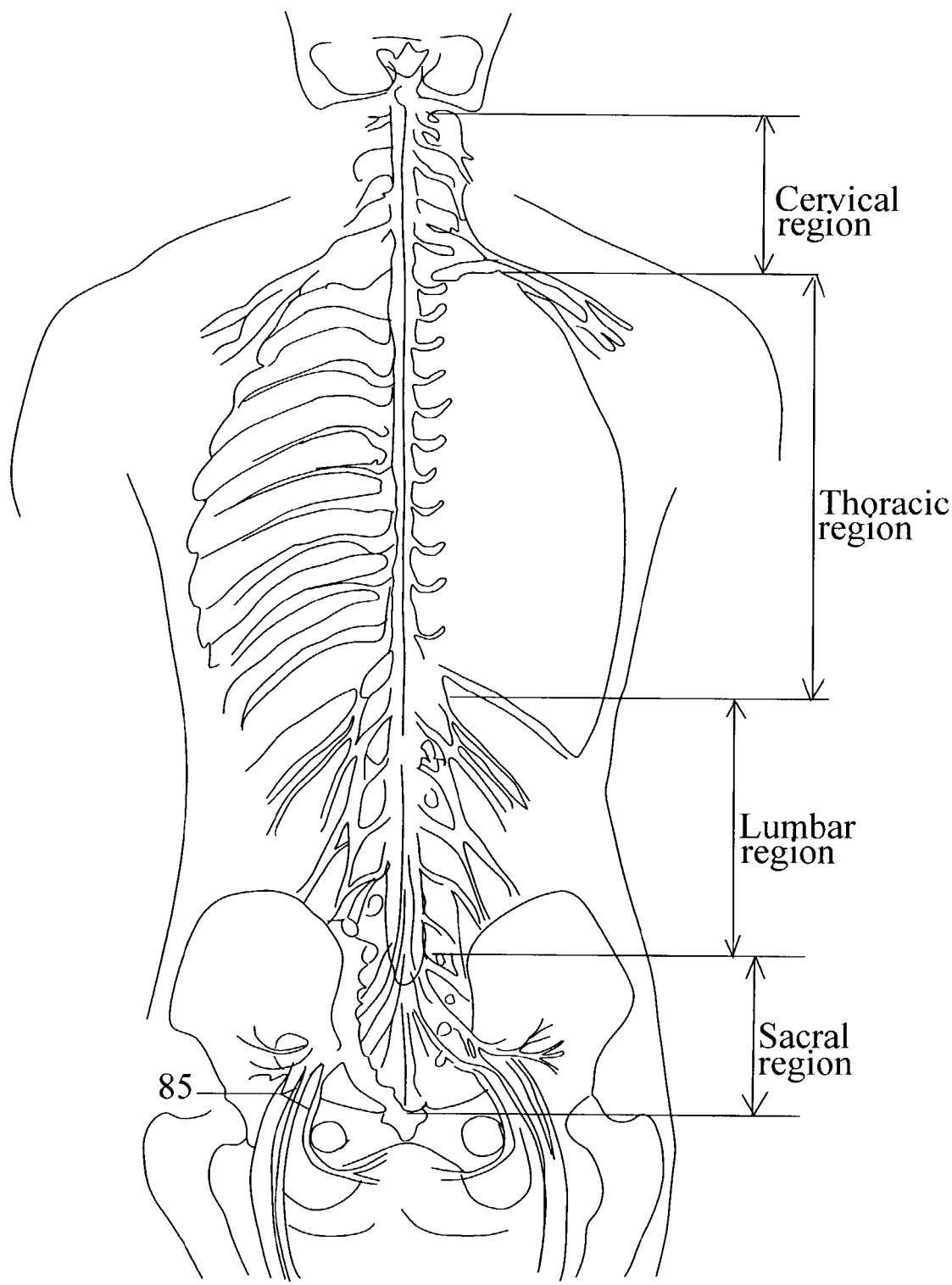
FIG. 3 is a diagram showing anatomic relationships of spinal nerves and sacral plexus.
Figure 4:
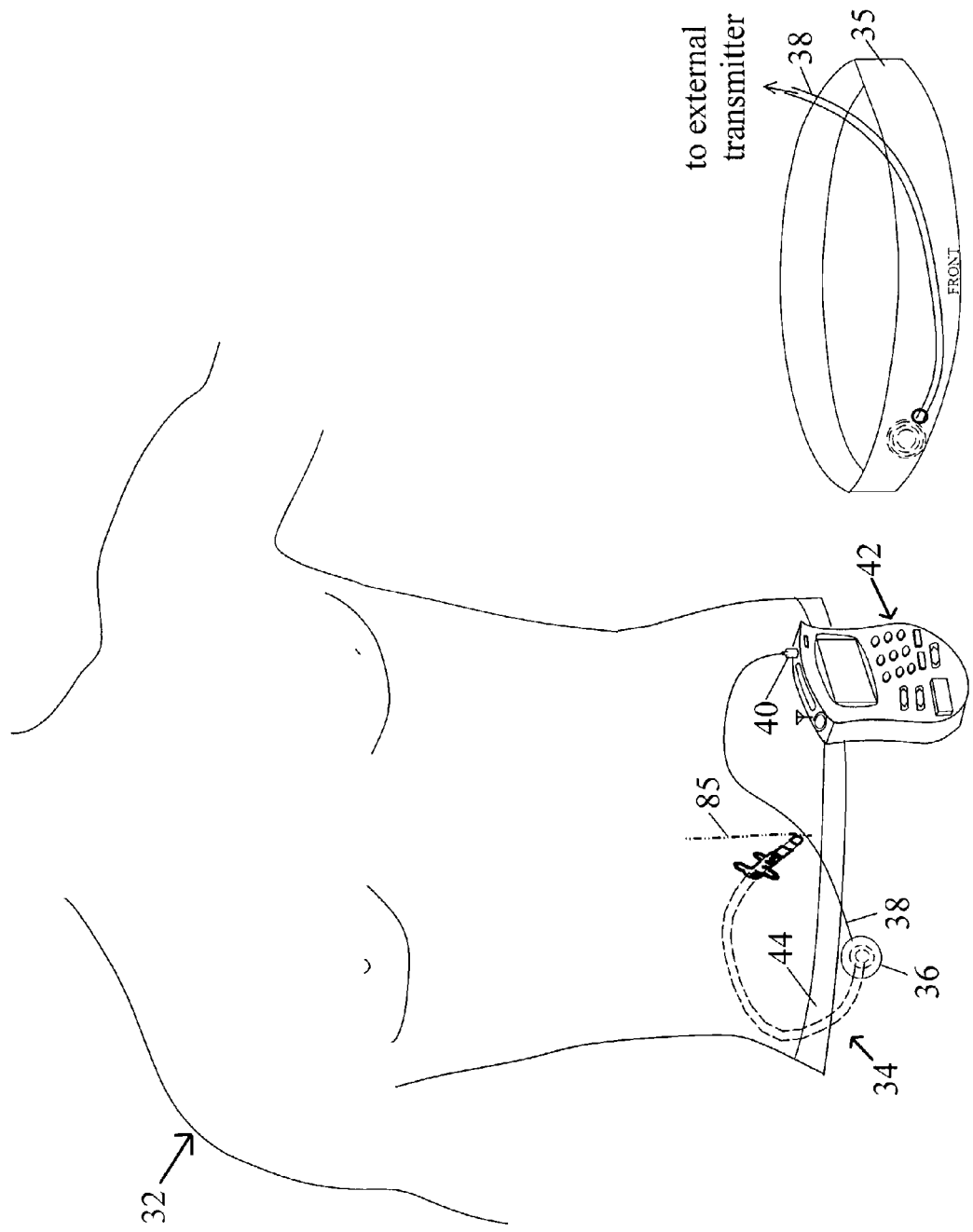
FIG. 4A is a diagram of a patient wearing an external stimulator (transmitter) on a belt.
FIG. 4B is a diagram showing a customized garment means for placing the primary (transmitting) coil in close proximity to the implanted (secondary) coil.

Referring now to the drawings, FIG. 4A shows a schematic diagram of a patient 32 with an implantable lead-receiver stimulator 34 and an external transmitter 42, clipped on to a belt 44 in this case. The external transmitter 42 may alternatively be placed in a pocket or other carrying device. The primary (external) coil(s) of the external transmitter 42 is inductively coupled to the secondary (implanted) coil of the implanted lead-receiver stimulator 34. As shown in FIG. 4B, a customized garment 35 may be worn by the patient 32 for keeping the primary coil(s) of the external transmitter 42 in close proximity to the subcutaneouly implanted secondary coil. In one embodiment, the system comprises proximity sensor circuitry to aid in placement of the external (primary) coil(s), as described later.

Figure 5:
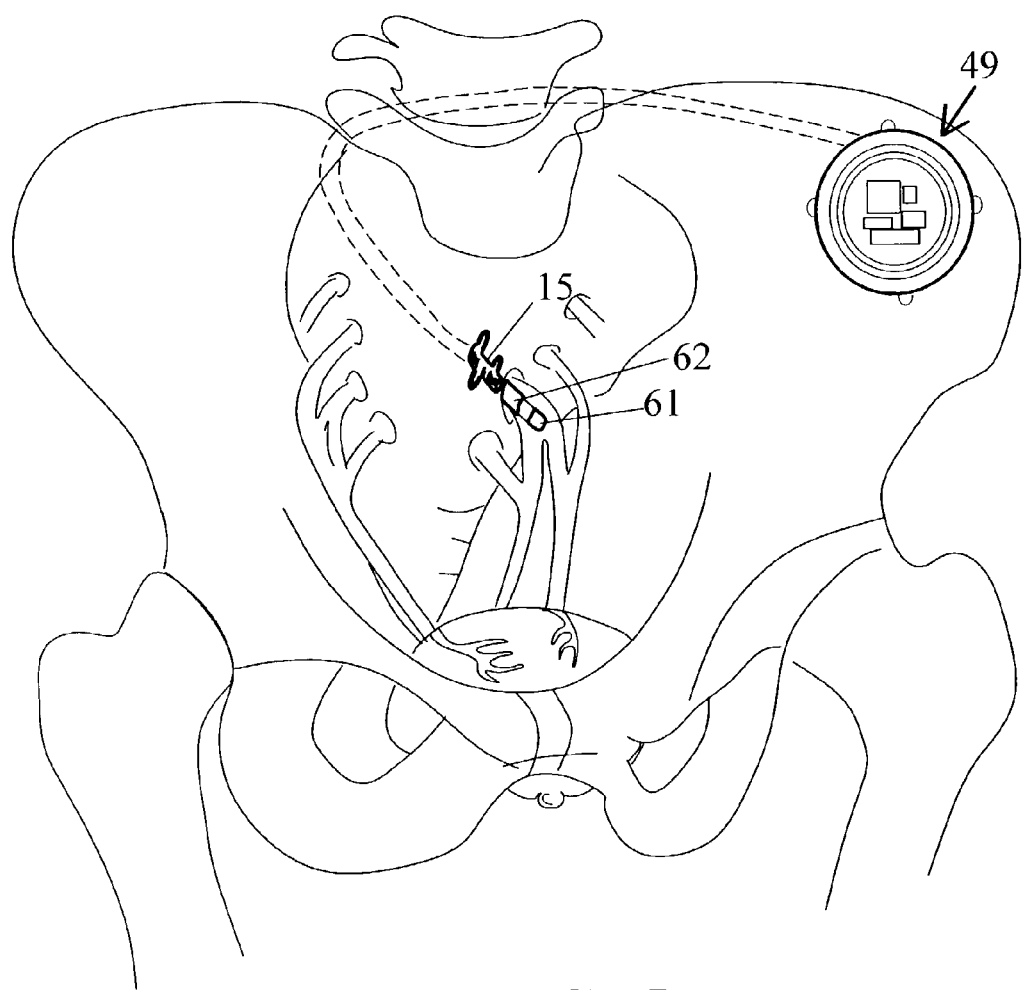
FIG. 5 is a diagram showing schematically the placement of the implanted lead in contact with the sacral nerve.

The implantable lead stimulus-receiver 34 has circuitry at the proximal end, and has two stimulating electrodes at the distal end. As shown in FIG. 5, the negative electrode (cathode) 61 is positioned at the distal end, and the positive electrode (anode) 62 is positioned away from the distal end 62, and is pulled back from the tip slightly. During the surgical implant procedure, the stimulating electrodes are tunneled subcutaneously and the electrodes are placed in the foraman of the sacral nerve 85 and the lead stimulus-receiver is implanted subcutaneously and held in place by tying sutures to the suture sleeve 15. The incisions are surgically closed and the chronic stimulation process can begin when the tissues are healed from the surgery.

Figure 6:
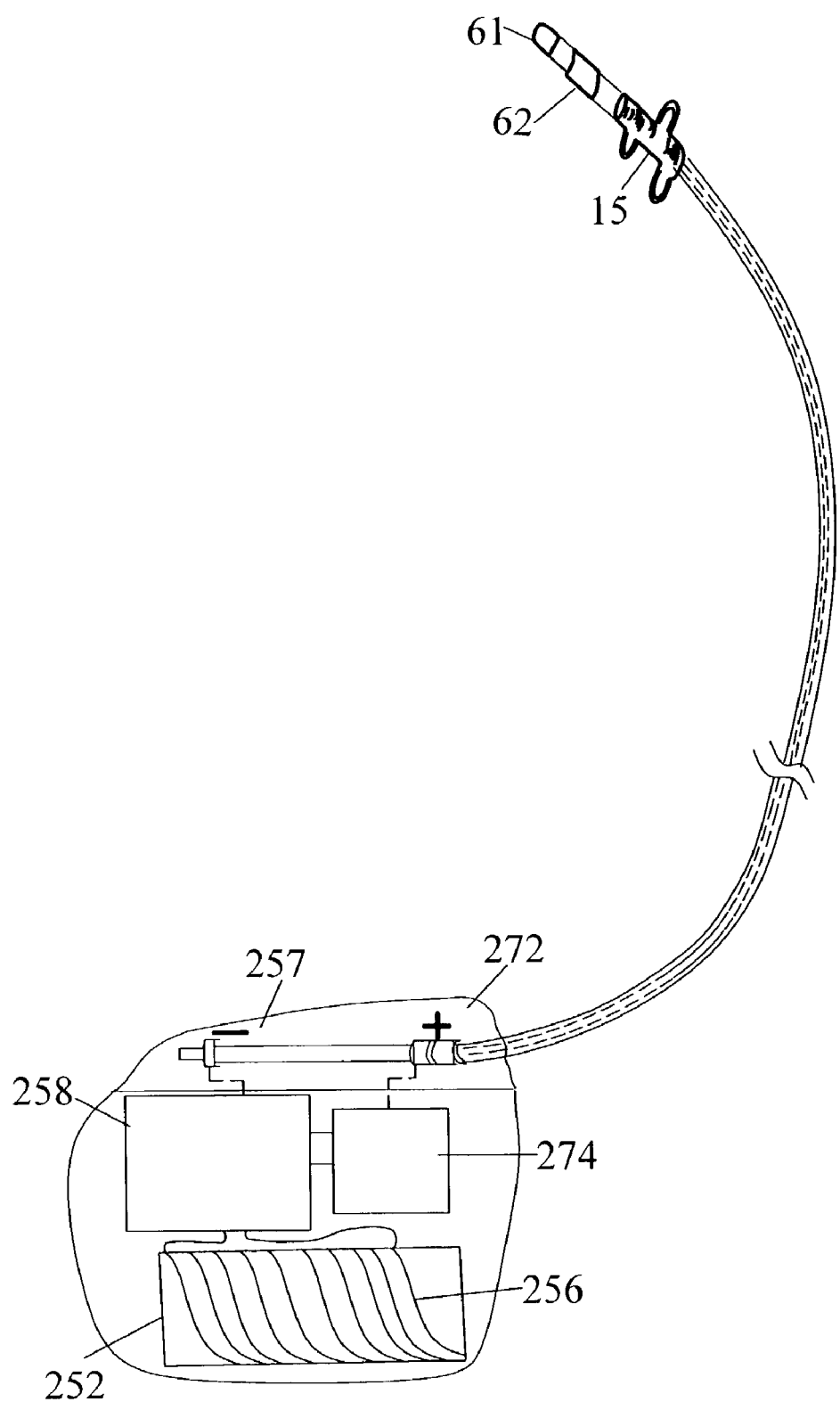
FIG. 6 is a schematic diagram showing the implantable lead stimulus-receiver.
Figure 7:
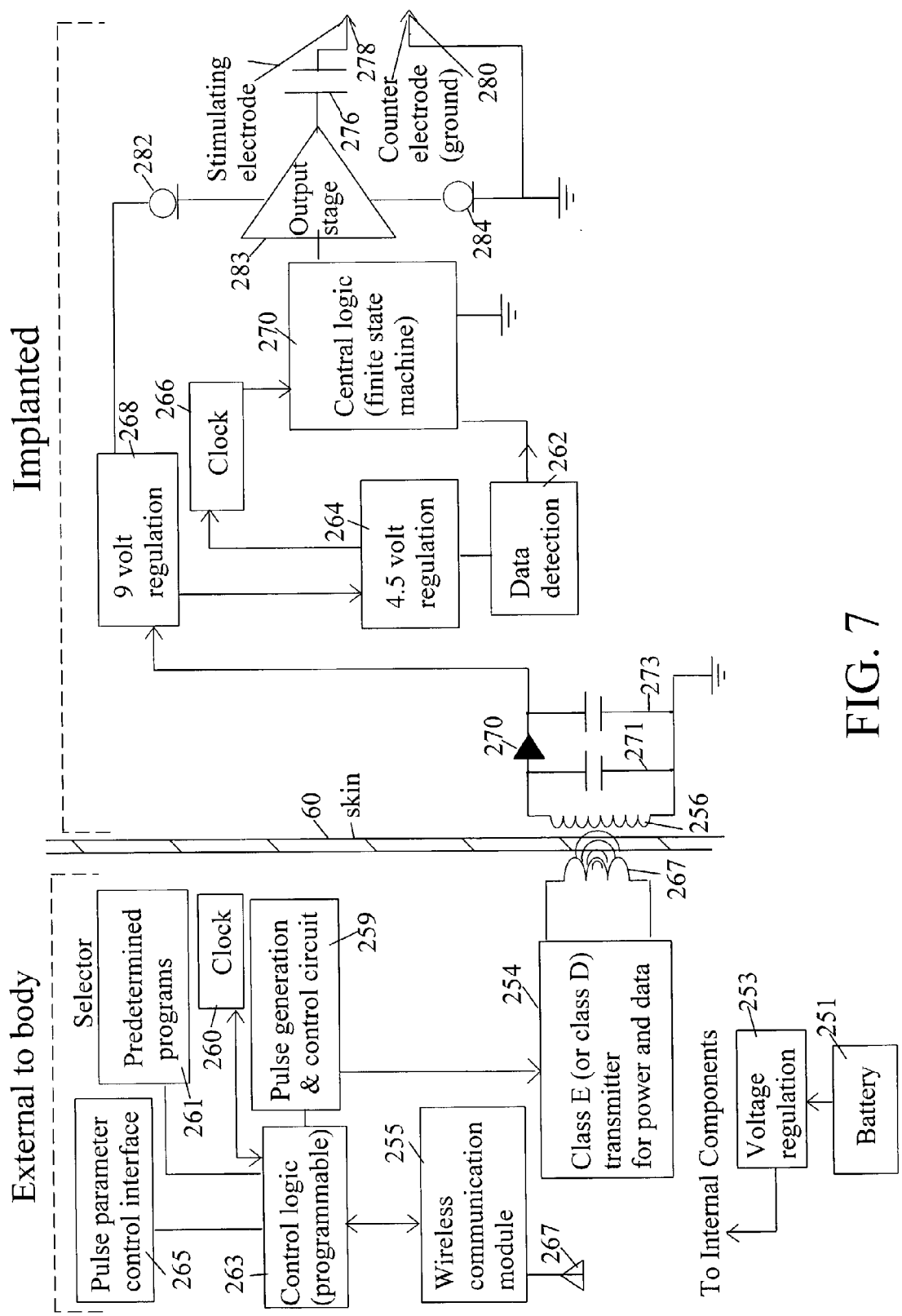
FIG. 7 is a block diagram showing schematically the functioning of the external transmitter and the implanted lead stimulus-receiver.

The presently preferred embodiment of the implanted lead stimulus-receiver and transmitter system are described in relation to FIG. 6 and FIG. 7. Other embodiments are also possible and are described later. In the presently preferred embodiment, as shown in FIG. 6, a solenoid coil 256 wrapped around a ferrite core 252 is used as the secondary of an air gap transformer for receiving power and data to the implanted device 34. The primary coil is external to the body. Since the coupling between the external transmitter coil 267 and receiver coil 256 may be weak, a high-efficiency transmitter/amplifier is used in order to supply enough power to the receiver coil 256. Class-D or Class-E power amplifiers may be used for this purpose, and are described later.

As shown in FIG. 7, the received signal after being picked by the resonant tank circuit comprising of inductor 256 and capacitor 271, goes through a rectifier 270. Even though a single diode 270 is shown in the figure, a diode bridge can be used for full-wave rectification, and the signal then goes through two series voltage regulators in order to generate the required supply voltages. The voltage regulators consist of rectifier, storage capacitor, and 4.5-V and 9-V shunt regulators implemented using Zenor diodes and resistors (not shown in FIG. 7). Bipolar transistors and diodes with high breakdown voltages are used to provide protection from high input voltages. Clock 266 is regenerated from the radio-frequency (RF) carrier by taking the peak amplitude of sinusoidal carrier input and generating a 4.5 V square wave output. Data detection circuitry is comprised using a low-pass filter (LPF), a high-pass filter (HPF), and a Schmitt trigger for envelope detection and noise suppression. The low-pass filter is necessary in order to extract the envelope from the high frequency carrier. Finally, the output circuit contains charge-balance circuitry, stimulus current regulator circuitry, and startup circuitry.

Figure 8:
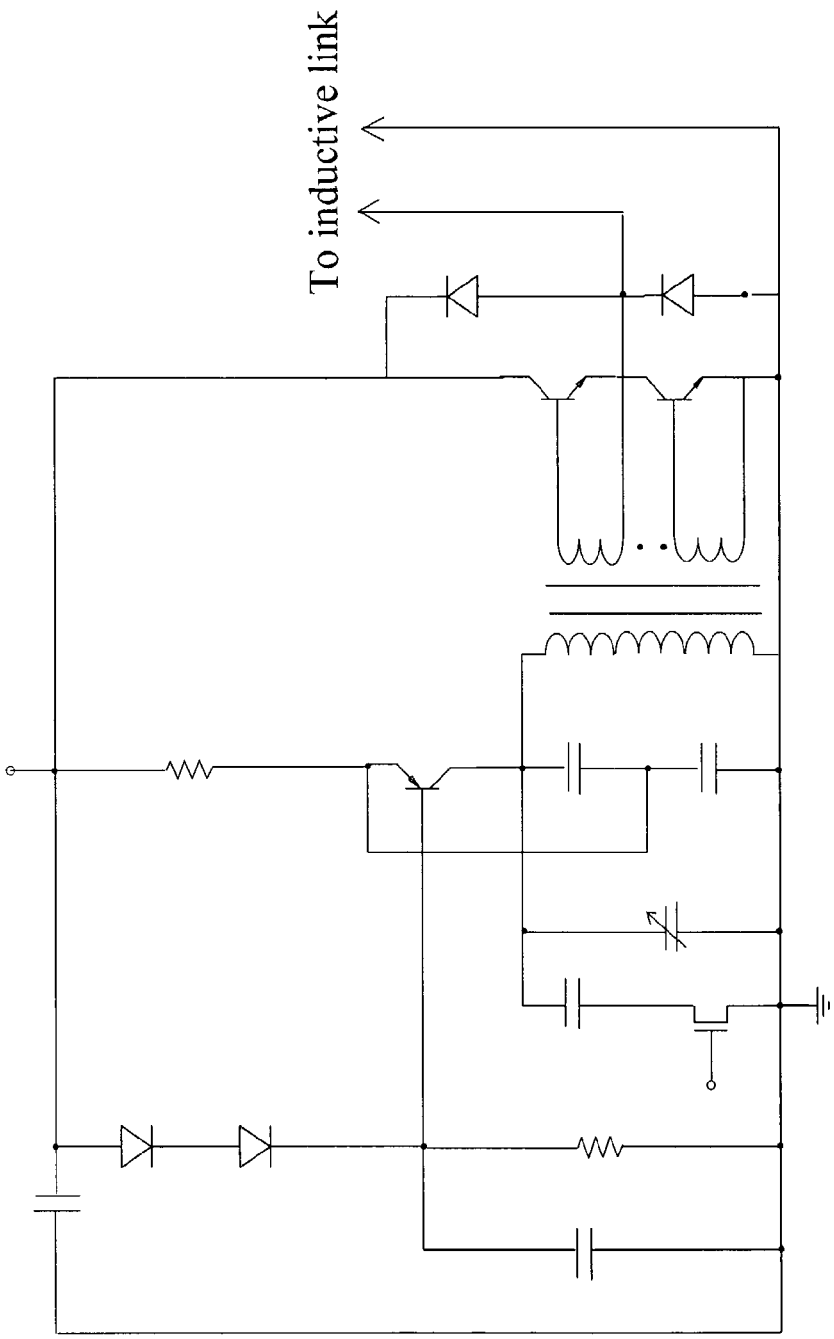
FIG. 8 is a schematic diagram showing a workable Class-D driver.

As shown in FIG. 7, a Class-D or Class E driver can be used in the external transmitter. A typical workable Class D driver is shown in FIG. 8. Class-D transmitter can drive the loads efficiently, and can supply a constant driving source so that the link output voltage, or current, remains stable. A Class-D transmitter can drive these loads efficiently because it can supply a constant source which is independent of the load. It simply switches the input of the link between the two terminals of the power supply. Reactive loads and load variation due to changing coupling should not affect its output level.

Figure 9A:
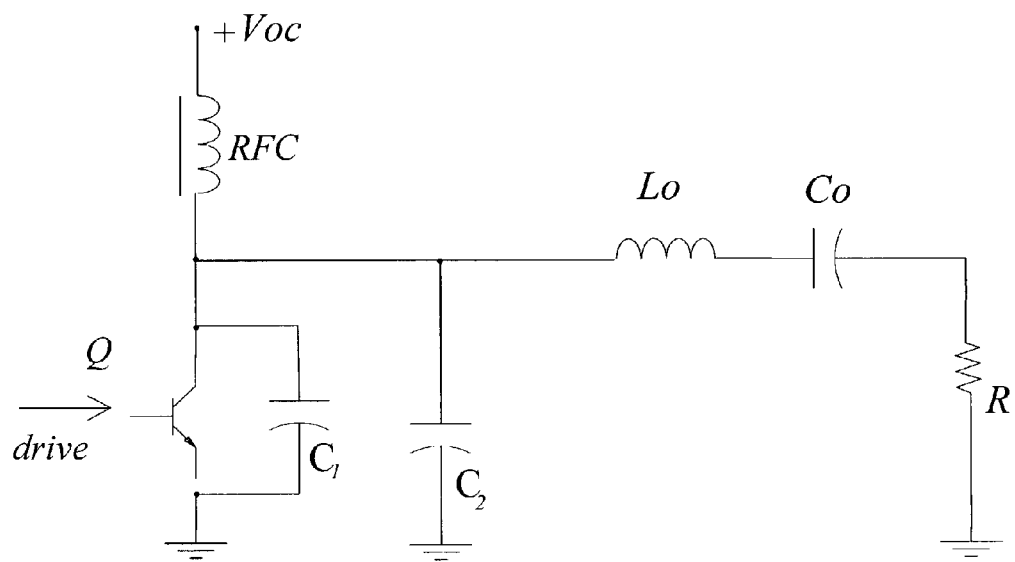
FIGS. 9A and 9B are electrical diagrams showing the concept of Class-E amplifier.
Figure 9B:
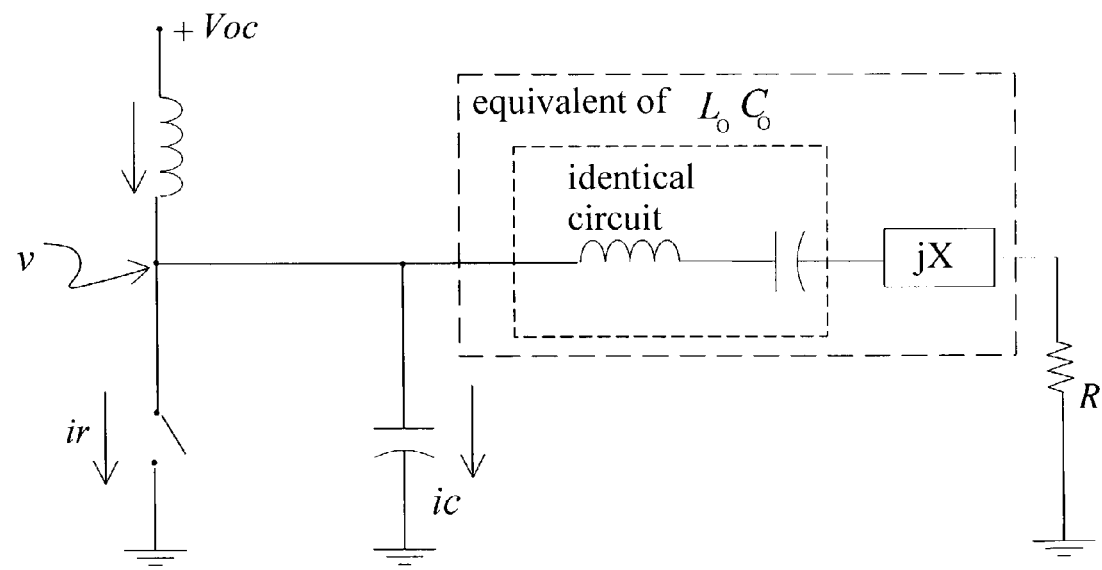
Figure 10:
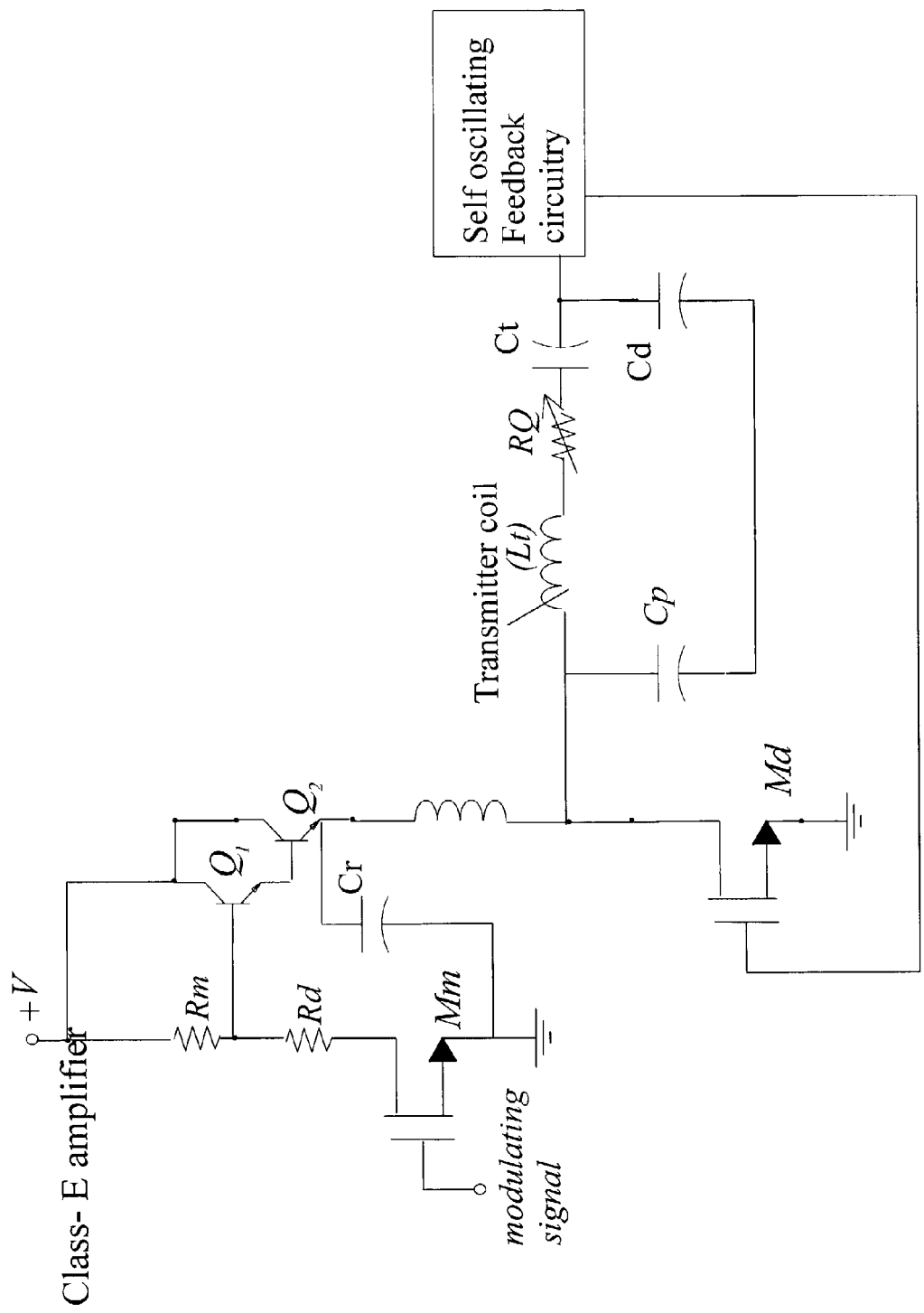
FIG. 10 is a schematic diagram showing a workable Class-E driver.

Even though both Class-D and Class-E transmitters are highly efficient, the Class-E operation of the presently preffered embodiment is explained in relation to FIGS. 9A, 9B, and 10. A basic circuit of Class-E amplifier is shown in FIG. 9A and its equivalent is shown in FIG. 9B. The "Class E" refers to a tuned power amplifier composed of a single-pole switch and a load network. The switch consists of a transistor or combination of transistors and diodes that are driven on and off at the carrier frequency of the signal to be amplified. In its most basic form, the load network consists of a resonant circuit in series with the load, and a capacitor which shunts the switch, FIGS. 9A and 9B. The total shunt capacitance is due to what is inherent in the transistor (C1) and added by the load network (C2). The collector or voltage waveform is then determined by the switch when it is on, and by the transient response of the load network when the switch is off.

In comparison, classes A, B, and C refer to amplifiers in which the transistors act as current sources; sinusoidal collector voltages are maintained by the parallel-tuned output circuit. If the transistors are driven hard enough to saturate, they cease to be current sources; however, the sinusoidal collector voltage remains. Class D is characterized by two (or more) pole switching configuration that define either a voltage current waveform without regard for the load network. Class D employs band-pass filtering. Table 1 below, compares the power and efficiency between different classes of amplifiers.

TABLE 1

| Class | $P_{max}$ | Efficiency | Comments |
|---|---|---|---|
| A | 0.125 | 50% | 360° conduction angle |
| B | 0.125 | 78.5% | 180° conduction angle |
| C | 0.0981 | 89.6% | 120° conduction angle |
| D | 0.318 | 100% | uses two devices with 1 A peak current |
| E | 0.0981 | 100% | Optimum 50% duty cycle |

Class E power amplifiers (as well as Class D and saturating Class C power amplifiers) might more appropriately be called power converters. In these circuits, the driving signal causes switching of the transistor, but there is no relationship between the amplitudes of the driving signal and the output signal. In Class E amplifiers, there is no clear source of voltage or current, as in classes A, B, C, and D amplifiers. The collector voltage waveform is a function of the current charging the capacitor, and current is function of the voltage on the load, which is in turn a function of the collector voltage. All parameters are interrelated. A typical workable Class-E driver is shown in FIG. 10.

Figure 11:
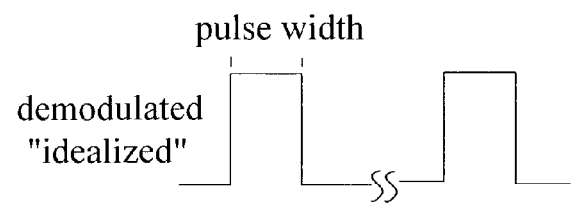
FIGS. 11A, 11B, and 11C are examples of "idealized" demodulated pulses delivered to the sacral nerve for neuromodulation.
Figure 11:
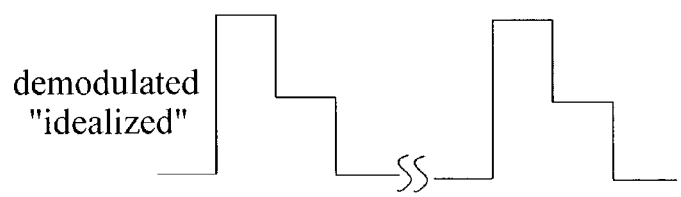
Figure 11:
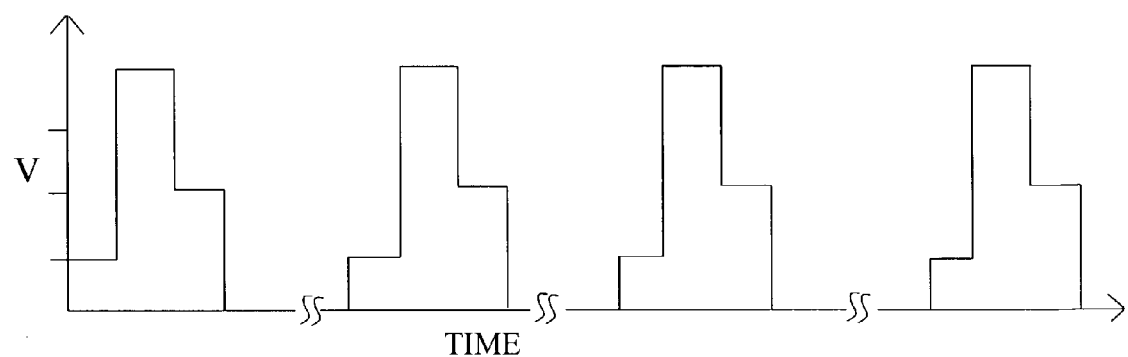

As shown in FIG. 7, the output of the implanted lead stimulus-receiver is delivered to the sacral nerve via stimulating electrodes 278, 280. Examples of resulting waveform used for modulating the sacral nerve are shown in FIGS. 11A, 11B, and 11C which show examples of "idealized" pulses delivered to the sacral nerve bundle for neuromodulation.

As also shown schematically in FIG. 7, the external pulse generator-transmitter can be operated via selecting a stored predetermined program 261 or by adjusting the stimulating program parameters individually 265. The range of electrical parameters that can be adjusted by the patient is defined by the attending physician, and parameters outside of that range are "locked out" to the patient via software. As also noted in FIG. 7, there is an optional wireless communications module 255 for remotely communicating with the external pulse generator-transmitter, as mentioned later and described more fully in a co-pending application.

Figure 12:
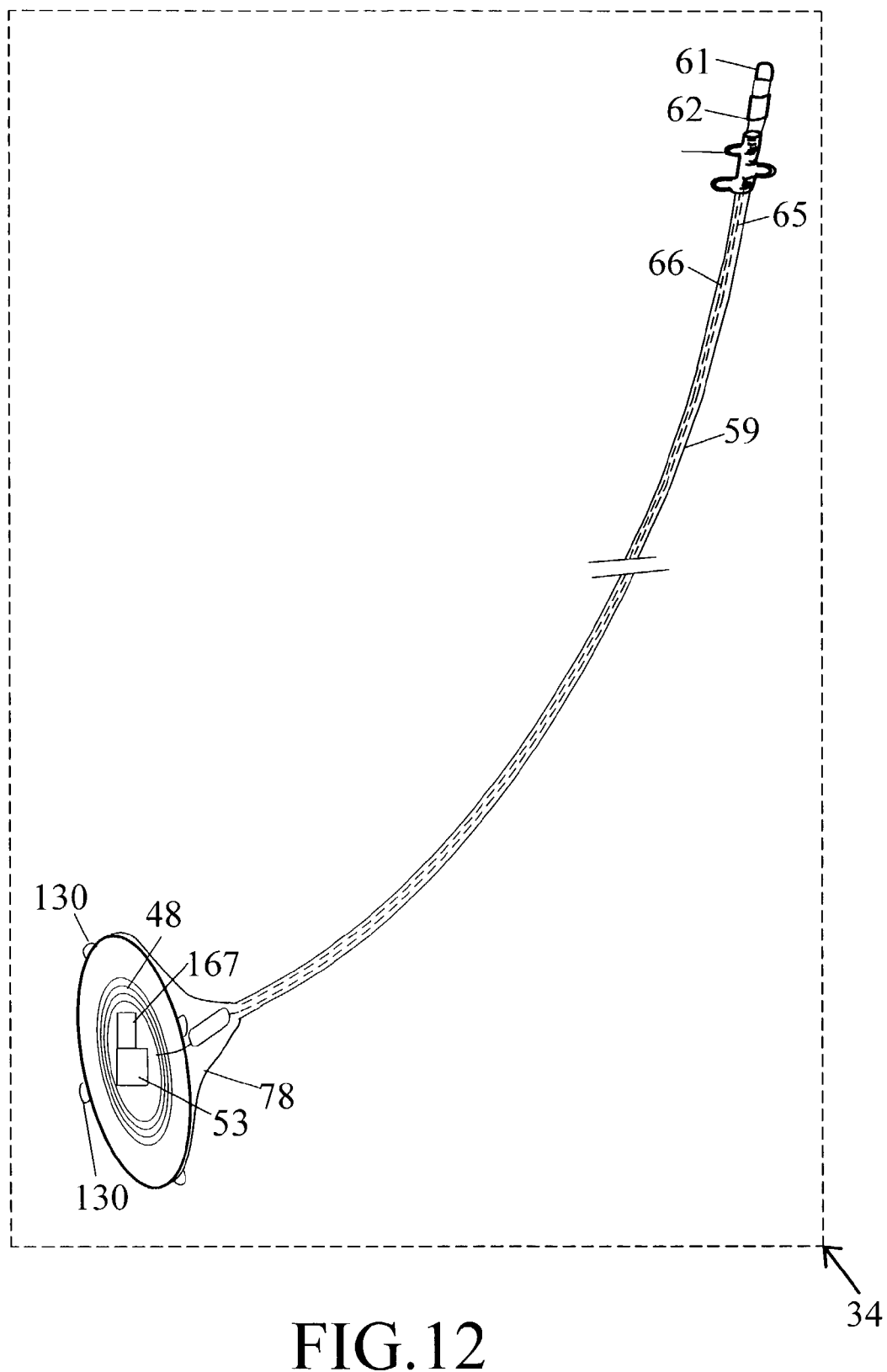
FIG. 12. is a diagram of the implanted lead stimulus-receiver for urinary incontinence.

An alternative embodiment, using only passive components in the implanted stimulus-receiver, and using flat "pancake" type coils for both the external (primary) and implanted (secondary) can also be used, and is described below. The implantable stimulus receiver 34 of this embodiment is shown in FIG. 12. In this embodiment, the external coil 46 is connected to proximity sensing circuitry 50 (shown in FIG. 13). The correct positioning of the external coil 46 with respect to the internal coil 48 is indicated by turning ON of a light emitting diode (LED) on the external stimulator 42.

Figure 13:
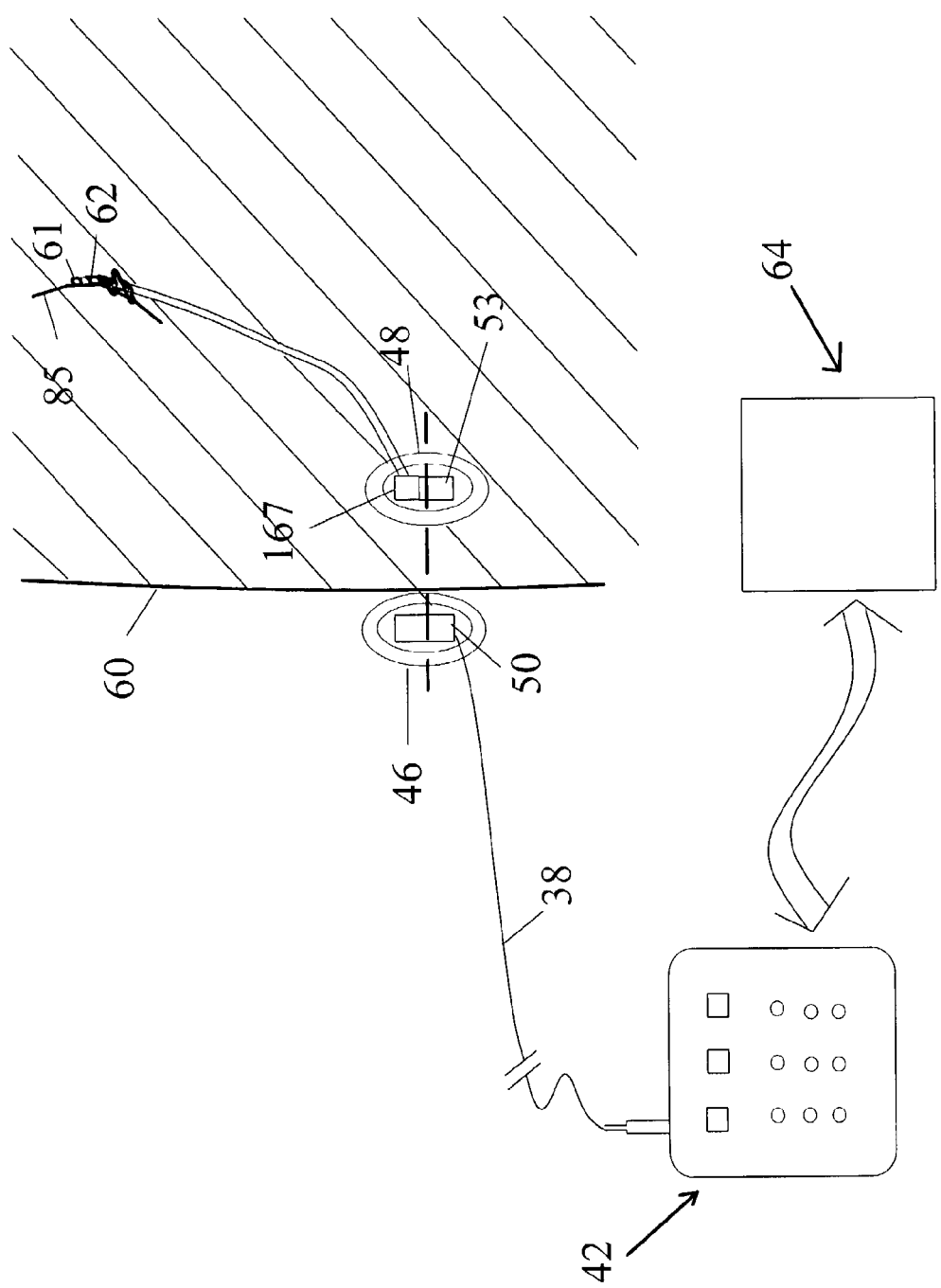
FIG. 13. shows external stimulator (transmitter) coupled to the implanted unit.

Optimal placement of the primary (external) coil 46 is done with the aid of proximity sensing circuitry incorporated in the system. The proximity sensing occurs utilizing a combination of external and implantable or internal sensing components. The internal components contains a relatively small magnet composed of materials that exhibit Giant Magneto-Resistor characteristics such as Samarium-cobalt, passive circuitry and a coil. As depicted in FIG. 13, the external coil 46 contains proximity sensor circuitry 50 that is rigidly connected in a convenient enclosure mounted supercutaneously. The sensors measure the direction of the field applied from the magnet to sensors within a specific range of field strength magnitude. The dual sensors exhibit accurate sensing under relatively large separation between the sensor and the target magnet. As the external coil 46 placement is "fine tuned", the condition where the supercutaneous external (primary) coil 46 comes in optimal position and is located adjacent and parallel to the subcutaneous (secondary) coil 48, along its axis, is recorded and indicated by a light emitting diode (LED) on the external stimulator 42.

Figure 14:
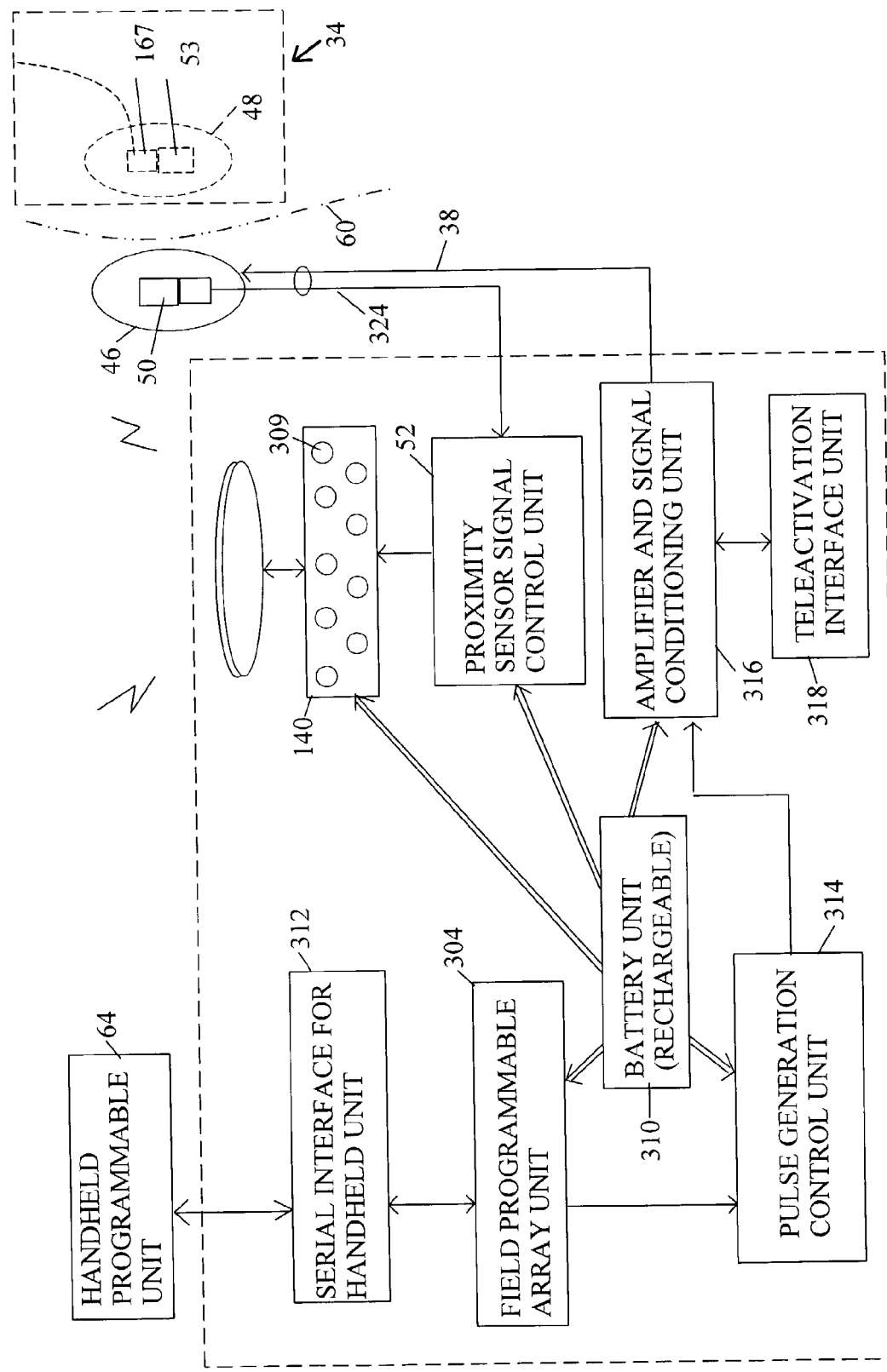
FIG. 14 shows the block diagram for the external stimulator.

FIG. 14 shows an overall block diagram of the external stimulator 42. The proximity sensing components are the primary (external) coil 46, supercutaneous (external) proximity sensors in the proximity sensor circuit unit 50, and a subcutaneous secondary coil 48 with a Giant Magneto Resister (GMR) magnet 53 associated with the proximity sensor unit. The proximity sensor circuit 50 provides a measure of the position of the secondary implanted coil 48. The signal output from proximity sensor circuit 50 is derived from the relative location of the coils. The coil sub-assemblies consist of the coil and the associated electronic components, that are rigidly connected to the coil.

The proximity sensors (external) contained in the proximity sensor circuit 50 detect the presence of a GMR magnet 53, composed of Samarium Cobalt, that is rigidly attached to the subcutaneous secondary coil 48. The proximity sensors are mounted externally as a rigid assembly and sense the actual separation between the coils, also known as the proximity distance. In the event that the distance exceeds the theoretical limit, the signal drops off and an alarm sounds to indicate failure of the production of adequate signal in the secondary implant circuit 167, as applied in the present embodiment of the device. This signal is provided to the location indicator LED 140. The programmable parameters are stored in a programmable logic 304.

Figure 15:
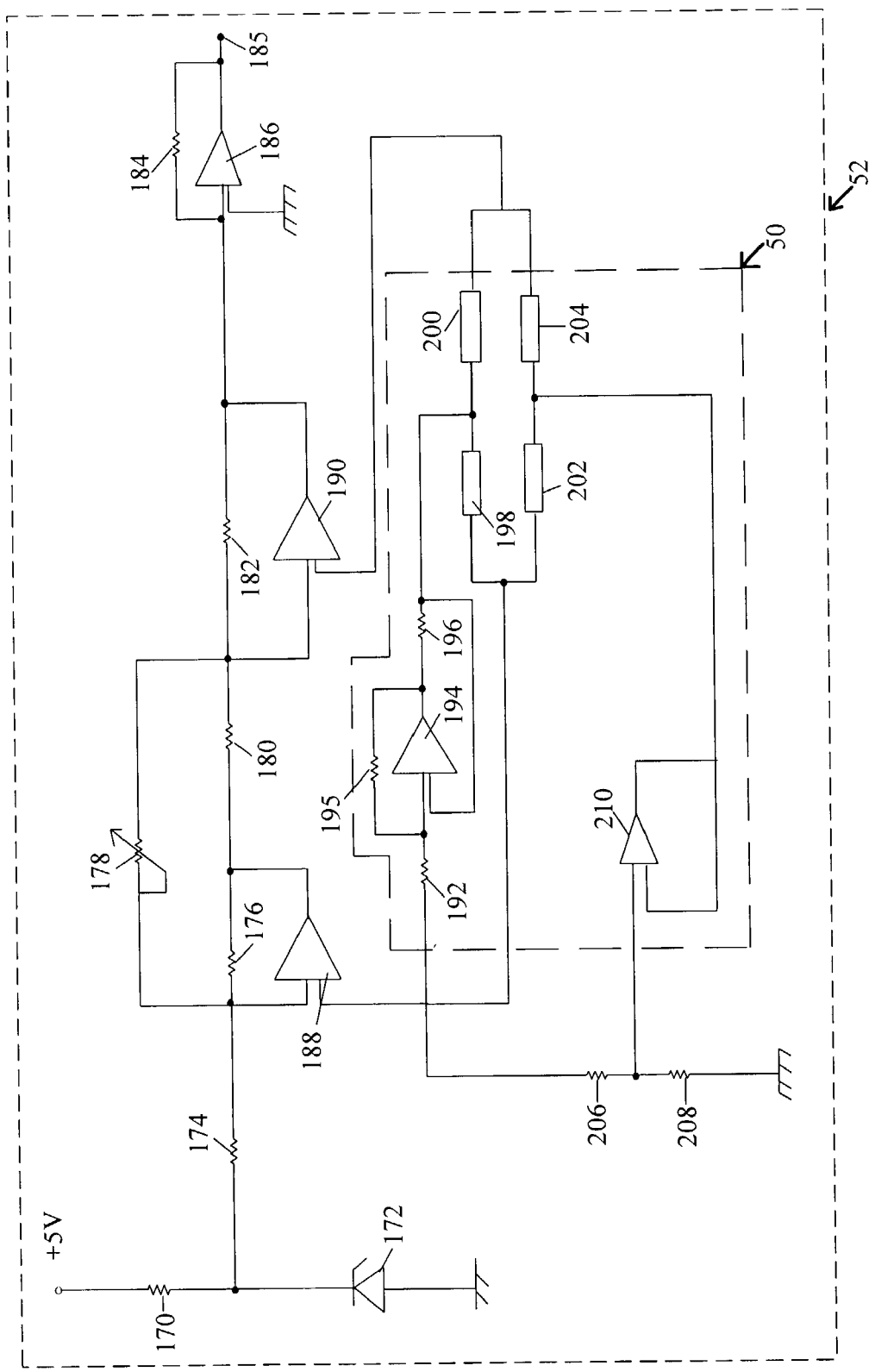
FIG. 15 shows the GMR sensor amplification unit.

FIG. 15 shows the circuit used to drive the proximity sensors of the proximity sensor circuit. The two proximity sensors 198, 202 obtain a proximity signal based on their position with respect to the implanted GMR magnet 53. This circuit also provides temperature compensation. The sensors 198, 202 are 'Giant Magneto Resistor' (GMR) type sensors packaged as proximity sensor unit 50. There are two components of the complete proximity sensor circuit 51. One component is mounted supercutaneously 50 and the other component is mounted in the remote control unit 42. The resistance effect depends on the combination of the soft magnetic layer of magnet 53, where the change of direction of magnetization from external source can be large, and the hard magnetic layer, where the direction of magnetization remains unchanged. The resistance of this sensor varies along a straight motion through the curvature of the magnetic field. A bridge differential voltage is suitably amplified and used as proximity signal.

The Siemens GMR B6 (Siemens Corp., Special Components Inc. New Jersey) is used for this function in the present embodiment. The maximum value of the peak-to-peak signal is observed as the external magnetic field becomes strong enough, at which point the resistance increases, resulting in the increase of the field-angle between the soft magnetic and hard magnetic material. The bridge voltage also increases. In this application, the two sensors 198, 202 are oriented orthogonal to each other.

The distance between the magnet and sensor is not relevant as long as the magnetic field is between 5 and 15 KA/m, and provides a range of distances between the sensors 198, 202 and the magnetic material 53. The GMR sensor registers the direction of the external magnetic field. A typical magnet to induce permanent magnetic field is approximately 15 by 8 by 5 $mm^3$, for this application and these components. However, the sensors 198, 202 are sensitive to temperature, such that the corresponding resistance drops as temperature increases. This effect is quite minimal until about 100° C. A full bridge circuit is used for temperature compensation, as shown in temperature compensation circuit 50 of FIG. 9. The sensors 198, 202 and a pair of resistors 200, 204 are shown as part of the bridge network for temperature compensation. It is also possible to use a full bridge network of two additional sensors in place of the resistors 200, 204.

The signal from either proximity sensor 198, 202 is rectangular if the surface of the magnetic material is normal to the sensor and is radial to the axis of a circular GMR device. This indicates a shearing motion between the sensor and the magnetic device. When the sensor is parallel to the vertical axis of this device, there is a fall off of the relatively constant signal at about 25 mm. separation. The GMR sensor combination varies its resistance according to the direction of the external magnetic field, thereby providing an absolute angle sensor. The position of the GMR magnet can be registered at any angle from 0 to 360 degrees.

The remote circuit package is shown in FIG. 14 and indicator unit 140 is provided to indicate following conditions: low battery state (if external battery is low), program number in use, proximity distance too large or coil proximity failure (for situations where the patch containing the external coil 46, has been removed, or is twisted abnormally etc.). Indication is also provided to assist the placement of the patch. In case of general failure, a red light with audible signal is provided when the signal is not reaching the subcutaneous circuit. The information on the low battery, normal and out of power conditions will forewarn the user of the requirements of any corrective actions.

Figure 16:
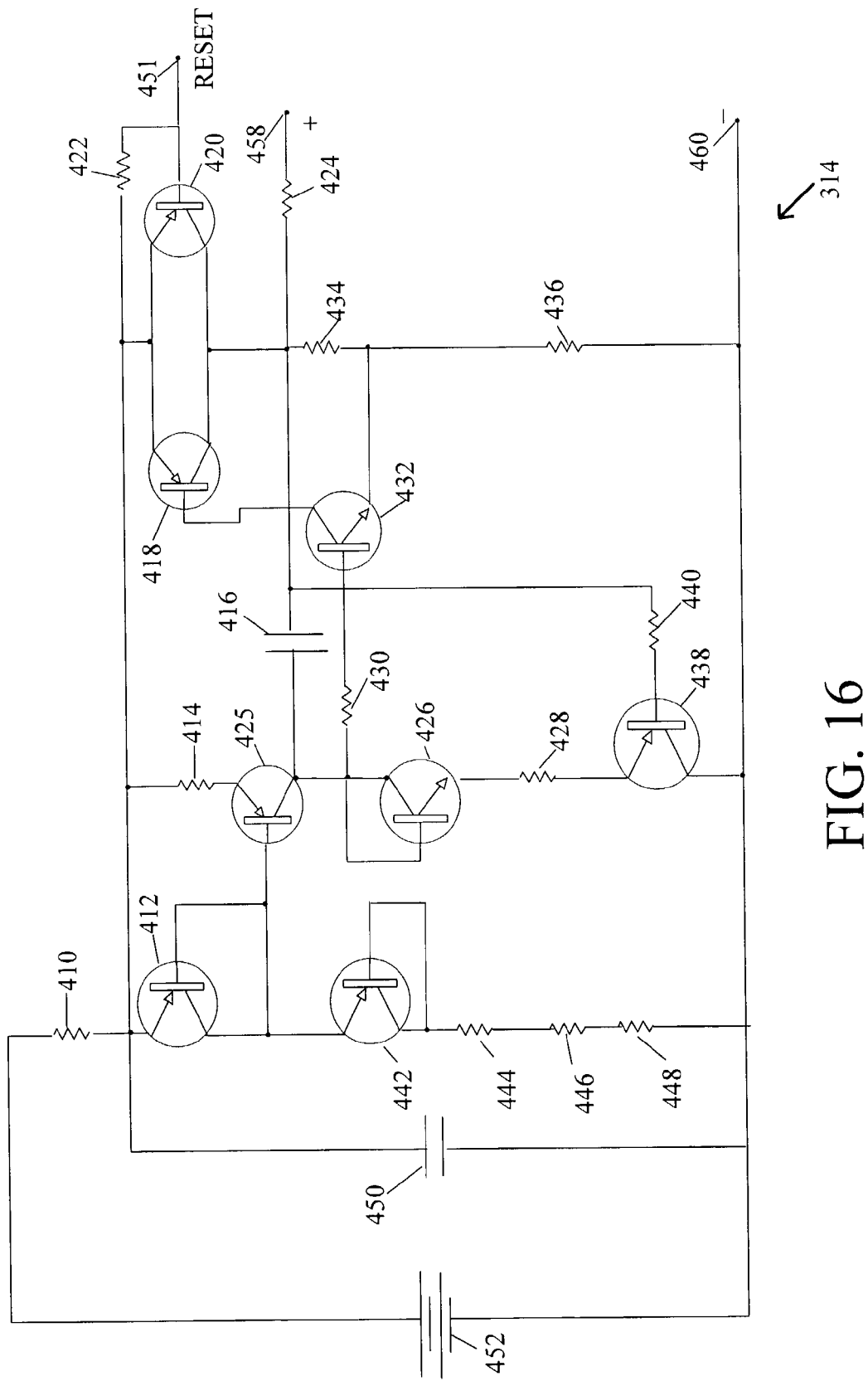
FIG. 16 shows the external pulse generator circuit.

The pulse generator circuitry, shown schematically in FIG. 16, exhibits typical multivibrator functionality. This circuit produces regularly occurring pulses where the amplitude, pulse width and frequency is adjustable. The battery 452 is the main external power source for this circuit and can derive from the rechargeable battery 310 (shown in FIG. 14). The capacitor 450 is connected in parallel with the battery 452. The combination of transistors 412, 442 and 425, and resistors 410, 444, 446 and 448 acts as a constant current source generated at the collector of transistor 426. The transistor 412 has collector connected to the emitter of transistor 442 and base of transistor 425. The transistors 412 and 442 are connected to provide a constant voltage drop. Likewise, transistor 426 also acts as a diode with a resistor 428 connected in series and further connected to the negative terminal of the line at terminal 460. Capacitor 416 provides timing characteristics and its value helps determine pulse width and pulse frequency. The output of the oscillator appears at terminal 458.

Initially, the capacitor 416 gets charged with current from the path of resistor 434 and 436 while all the transistors are turned off. As the capacitor charges up transistor 432 will become forward biased and current will flow via resistors 430 and 436 from the base to emitter resistors. This action turns on the transistor 418 and the positive voltage from the power supply 452 is made available at the base of transistor 438 through resistor 440. This results in the transistor 438 getting turned on. The conduction of transistor 438 causes capacitor 416 to discharge. The time constant for the charge and discharge of capacitor 416 is determined by value of the resistors 428 and 440 and capacitor 416. After the time constant, transistor 432 turns off, and this in turn turns off transistors 438 and 418. A reset mechanism for this multivibrator can be provided by setting a positive voltage, for example 2.5 volts, to the base of transistor 420. This positive increase in voltage turns on transistor 420 followed by transistor 438. The turning on of transistor 438 discharges the capacitor 416 and the reset operation is complete.

Figure 17:
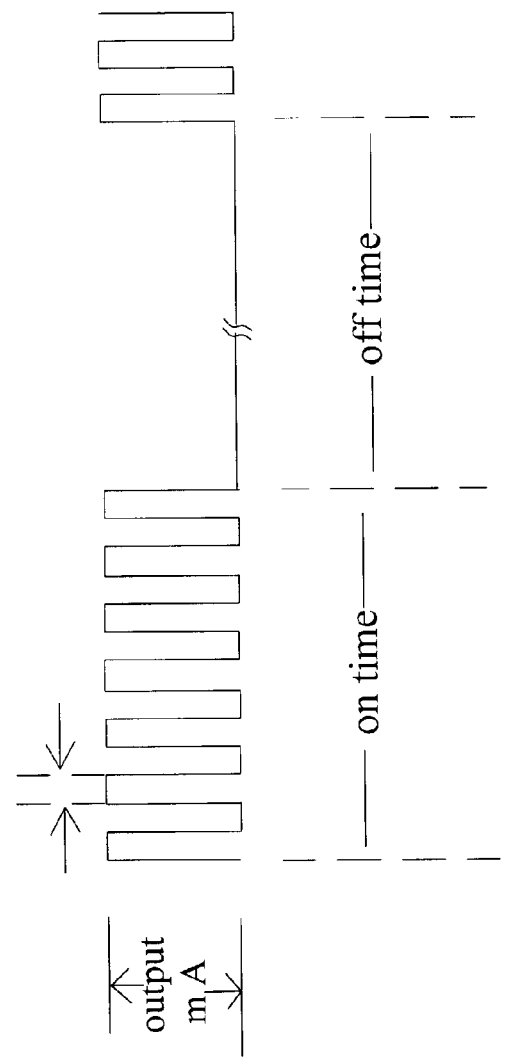
FIG. 17A shows an example of the pulse train.
FIG. 17B shows the ramp-up and ramp-down characteristic of the pulse train.
Figure 17:
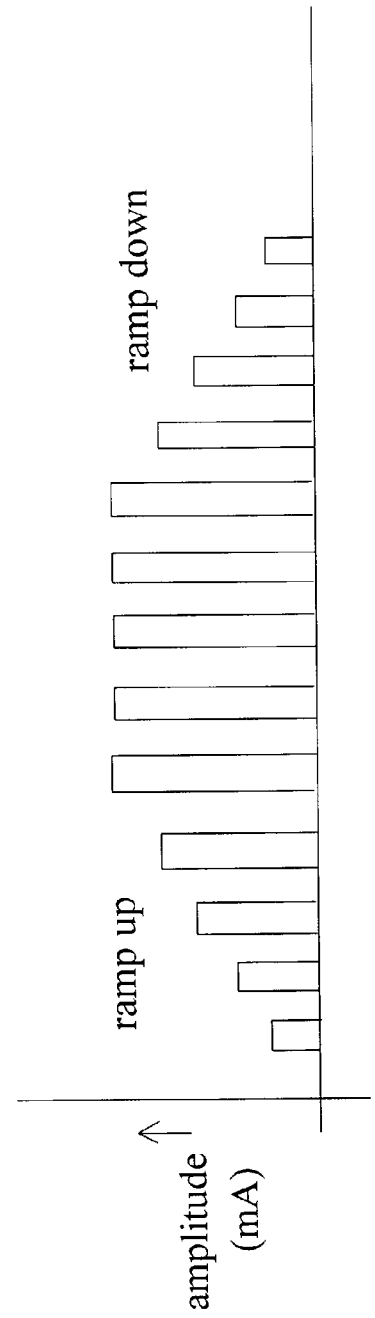

FIG. 17A shows graphically the "idealized" pulses delivered to the nerve tissue for therapy. As shown in FIG. 17B, for patient comfort when the electrical stimulation is turned on, the electrical stimulation is ramped up and ramped down, instead of abrupt delivery of electrical pulses.

The external stimulator 42 contains several predetermined programs that comprise a unique combination of pulse amplitude, pulse width, frequency of stimulation, ON time and OFF time. The various predetermined programs represent varying degrees of aggressiveness of the stimulation therapy. At least one of these programs may be "locked-out" to the patient. The physician can activate the patient "locked out" programs, either in person by accessing the programs via a handheld programmable unit 64, or activate the programs remotely via the internet cable connection as described in a copending application. The number of predetermined programs can be as many as 50 programs, and such a number is considered within the scope of the invention. In order to keep the number of programs convenient for the patient, the presently preferred embodiment contains nine predetermined programs that are arranged in such a way that the aggressiveness of the stimulation (therapy) increases from program #1 to program #2 and so on.

The following are examples of least aggressive therapy.

Program: 1.5 volt output, 0.2 msec pulse width, 10 Hz frequency, 30 sec ON time, 30 sec OFF time, in repeating cycles.

Program: 2.0 volt output, 0.2 msec pulse width, 15 Hz frequency, 1 minute ON time, 30 sec OFF time, in repeating cycles.

The following are examples of more aggressive level of therapy.

Program: 2.5 volt output, 0.25 msec pulse width, 20 Hz frequency, continuously ON.

Program: 2.5 volt output, 0.3 msec pulse width, 30 Hz frequency, 30 sec ON time, 30 sec OFF time, in repeating cycles.

The following are examples of patient "locked-out" programs.

Program: 3.5 volt output, 0.25 msec pulse width, 25 Hz frequency, 5 minutes ON time, 1 minute OFF time, in repeating cycles.

Program: 4.5 volt output, 0.3 msec pulse width, 30 Hz frequency, 2 minutes ON time, 2 minutes OFF time, in repeating cycles.

The above are examples of the predetermined programs for urinary incontinence applications. The actual parameter settings for any given patient may deviate somewhat from the above.

In addition to the use of predetermined programs, a second method is to "custom" program the electrical parameters which can be selectively programmed, for specific disease state of the individual patient. The electrical parameters which can be individually programmed, include variables such as pulse amplitude, pulse width, frequency of stimulation, modulation type, modulation index, stimulation on-time, and stimulation off-time. Table two below defines the approximate range of parameters,

TABLE 2

Electrical parameter range delivered to the nerve

| PARAMER | RANGE |
|---|---|
| Pulse Amplitude | 0.1 Volt–10 Volts |
| Pulse width | 20 µS–5 mSec. |
| Frequency | 5 Hz–200 Hz |

TABLE 2-continued

Electrical parameter range delivered to the nerve

| PARAMER | RANGE |
|---|---|
| On-time | 10 Secs–24 hours |
| Off-time | 10 Secs–24 hours |

It being understood that the signals generated by the external pulse generator and transmitted via the primary coil 46 (antenna) are larger, because the attenuation factor between the primary coil and secondary coil is approximately 10–20 times, depending upon the distance, and orientation between the two coils. Accordingly, the range of transmitted signals of the pulse generator are approximately 10–20 times larger than shown in Table 2.

Figure 18:
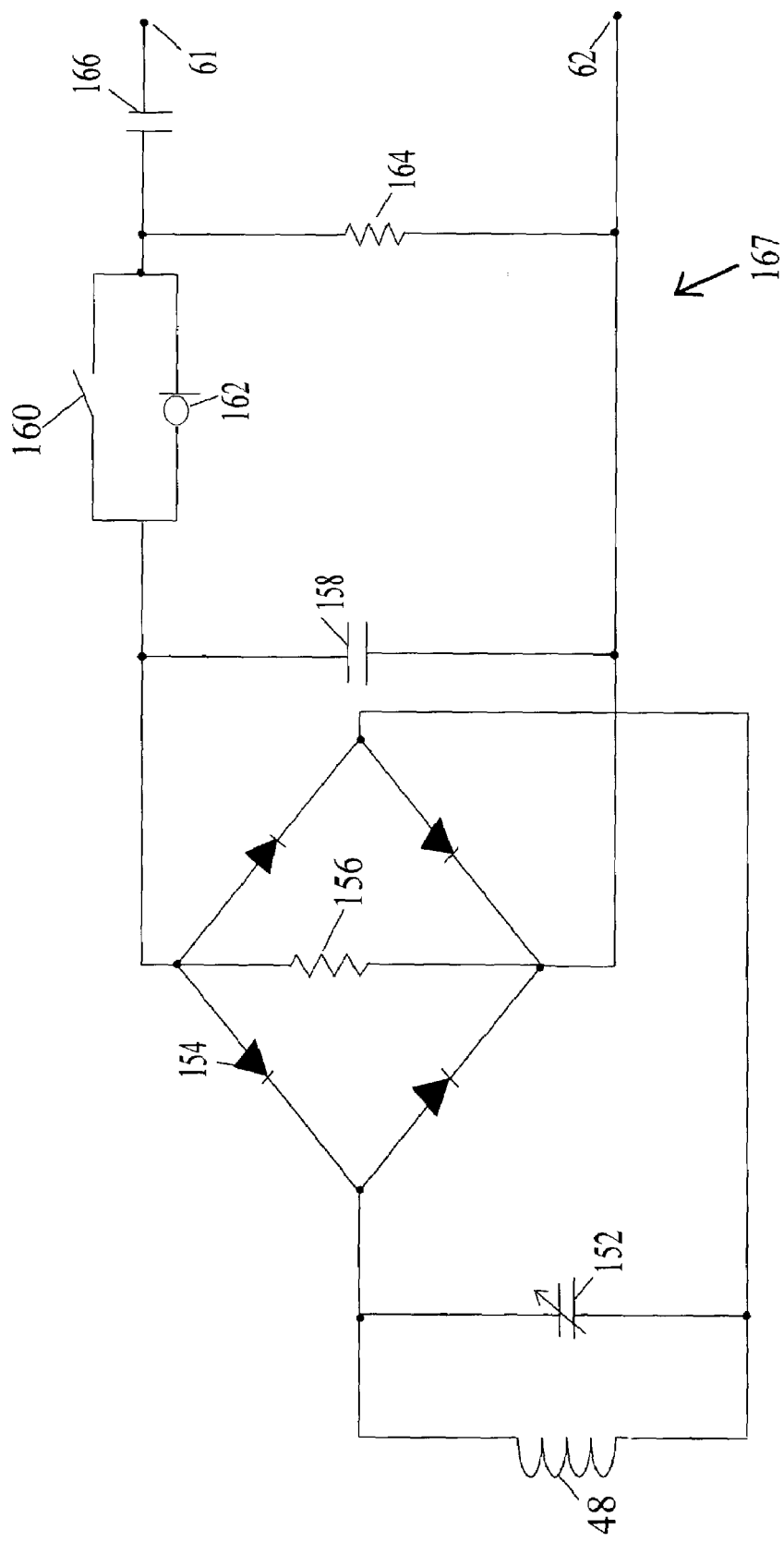
FIG. 18 is a schematic of the passive circuitry in the implanted lead stimulus-receiver.

The circuitry contained in the proximal end of the implantable lead-receiver 34 is shown schematically in FIG. 18. In this embodiment, the circuit uses all passive components. Approximately 25 turn copper wire of 30 gauge thickness is used for the primary coil 46 and secondary coil 48. This wire is concentrically wound with the windings all in one plane. A variable capacitor 152 provides flexibility in tuning to the actual frequency received by coil 48 from the primary coil 46. The frequency of the pulse-waveform delivered to the implanted coil 48 can vary and so a variable capacitor 152 provides ability to tune secondary implanted circuit 167 to the signal from the primary coil 46. The pulse signal from implanted coil 48 is rectified by the diode bridge 154 and frequency reduction obtained by capacitor 158 and resistor 164. The last component in line is capacitor 166, used for isolating the output signal from the electrode wire. The return path of signal from cathode 61 will be through anode 62 placed in proximity to the cathode 61 for "Bipolar" stimulation. In the current embodiment bipolar mode of stimulation is used, however, the return path can be connected to the remote ground connection (case) of implantable circuit 167, providing for much larger intermediate tissue for "Unipolar" stimulation. The "Bipolar" stimulation offers localized stimulation of tissue compared to "Unipolar" stimulation, and is therefore used in the current embodiment. Unipolar stimulation is more likely to stimulate skeletal muscle in addition to nerve stimulation. The implanted circuit 167 in this embodiment is passive, so a battery does not have to be implanted. It is however possible to implant a battery source for use of active component logic in the implant.

FIG. 12 shows a diagram of the implanted lead-receiver 34 adapted for sacral stimulation. The proximal end 49 is a relatively flat portion and contains the components shown in FIG. 18 on a printed circuit board. The distal end has the two electrodes 61 and 62 for stimulating the nerve. The passive circuitry and electrodes are connected by electrically insulated wire conductors running in the lead body 59 which is made of reinforced medical grade silicone in the presently preferred embodiment.

The fabrication of the lead-receiver 34 is designed to be modular. Thus, several different combinations of the components can be packaged without significantly altering the functionality of the device. As shown in FIG. 12, the lead-receiver 34 components are the proximal end 49 containing coil 48, electrical circuitry 167, and case 78, the lead body 59 containing the conductor 65,66 and the distal end has two electrodes cathode 61 and anode 62. In the modular design concept, several design variables are possible, as shown in the table below.

Table of lead-receiver design variables

| Proximal End | | | | | Distal End | |
|---|---|---|---|---|---|---|
| Circuitry and Return Electrode | Lead body-Lumens | Lead body-Insulation Materials | Lead-Coating | Conductor (connecting proximal and distal ends) | Electrode-Material | Electrode-Type |
| Bipolar | Single | Polyurethane | | Alloy of Nickel-Cobalt | Pure Platinum | Standard ball electrode |
| Unipolar | Double | Silicone | Antimicrobial | | Platinum-Iridium (Pt/IR) Alloy | Steroid eluting |
| | Coaxial | Silicone with Polytetra-fluoroethylene (PTFE) | Anti-Inflamatory | | Pt/Ir coated with Titanium Nitride | |
| | | | | | Carbon | |

Either silicone or polyurethane is a suitable material for the implantable lead-receiver body 59. Both materials have proven to have desirable qualities which are not available in the other. Permanently implantable pacemaker leads made of polyurethane are susceptible to some forms of degradation over time. The identified mechanisms are Environmental Stress Cracking (ESC) and Metal Ion Oxidation (MIO). Silicone on the other hand is a softer material, therefore lead body has to be made bigger. In the presently preferred embodiment silicone re-enforced with polytetrafluroethyene (PTFE) is used.

Nerve-electrode interaction is an integral part of the stimulation system. As a practical benefit of the modular design, any type of electrode described below can be used as the distal stimulating electrodes, without changing fabrication methodology or procedure significantly. In the presently preferred embodiment, electrodes made of platinum are used even though platinum-iridium alloys (such as 90% platinum-10% Iridium or 80% platinum-20% Iridium), or carbon could be used as the electrode material. The electrode type could be a hydrogel electrode or a steroid eluting electrode. In a steroid eluting electrode, a small amount of dexamethasone is placed either inside the distal electrode or around the electrode in a silicone collar. Approximately 1 mg dexamethasone is all that is required for the anti-inflammatory action, to lead to a thinner fibrous capsule, and therefore more efficient energy transfer from the electrode to the nerve tissue.

The conductor connecting the circuitry to the stimulating electrodes is made of an alloy of nickel-cobalt. The finished lead body may be coated with anti-inflammatory or anti-microbial coating to promote better healing after the surgical implant procedure. The coating is independent of fabrication and is performed after the lead-receiver assembly is completed.

Figure 19:
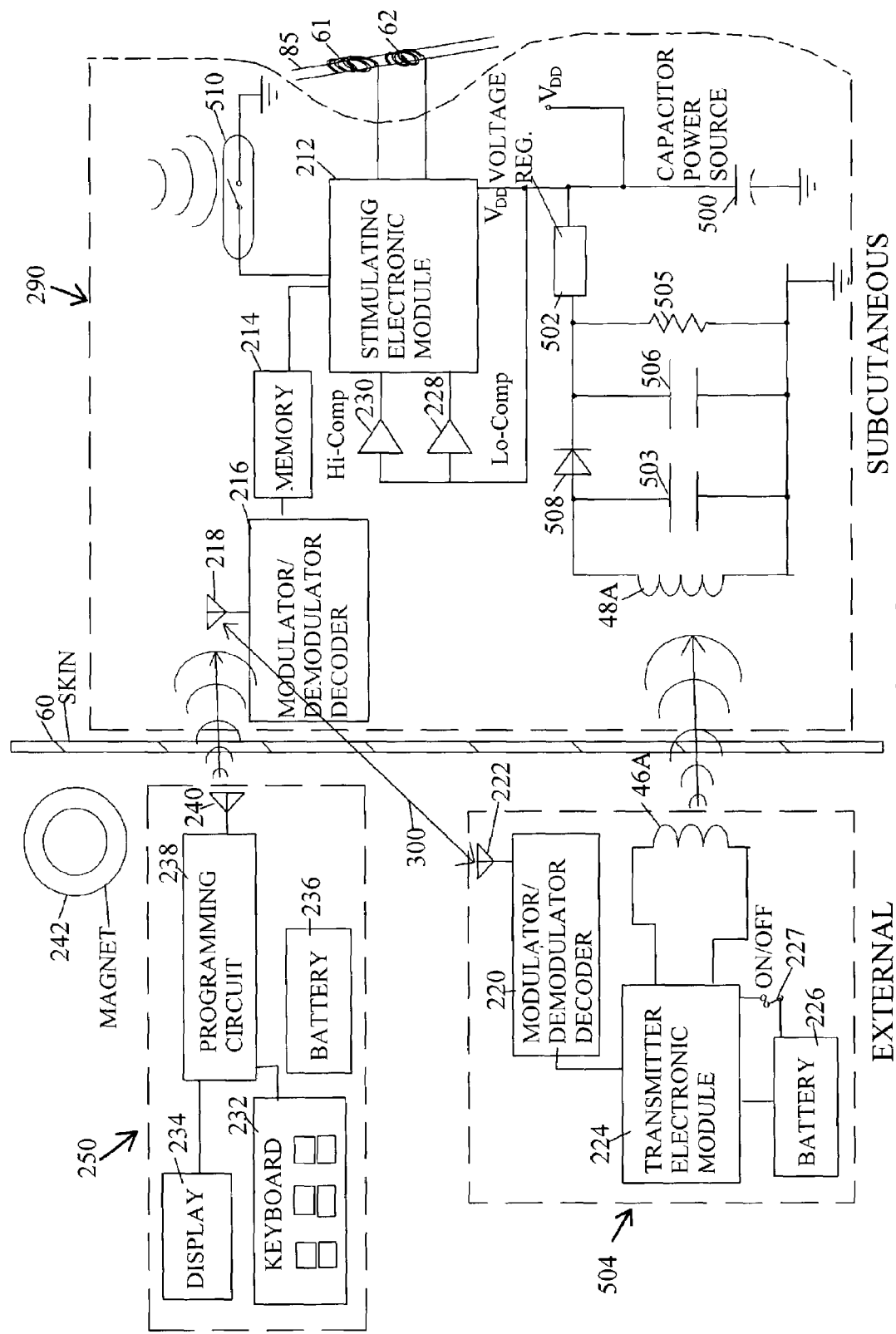
FIG. 19 is a schematic block diagram showing a system for neuromodulation of the sacral nerve with an implanted component which is both RF coupled and contains a power storage means.

In an extension of the above embodiment, another embodiment utilizing high value capacitors for storing charge described here, can also be used. In such a case, where the implanted lead-stimulator contains a high value, small sized capacitors for storing charge and delivering electric stimulation pulses for up to several hours by itself, once the capacitors are charged. As shown in FIG. 19 of the implanted stimulator 290 and the system, the receiving inductor 48A and tuning capacitor 503 are tuned to the frequency of the transmitter. The diode 508 rectifies the AC signals, and a small sized capacitor 506 is utilized for smoothing the input voltage $V_I$ fed into the voltage regulator 502. The output voltage $V_D$ of regulator 502 is applied to capacitive energy power supply and source 500 which establishes source power $V_{DD}$. Capacitor 500 is a big value, small sized capacative energy source which is classified as low internal impedance, low power loss and high charge rate capacitor, such as Panasonic Model No. 641.

The refresh-recharge transmitter unit 504 includes a primary battery 226, an ON/Off switch 227, a transmitter electronic module 224, an RF inductor power coil 46A, a modulator/demodulator 220 and an antenna 222.

When the ON/OFF switch is on, the primary (external) coil 46A is placed in close proximity to skin 60 and secondary coil 48A of the implanted stimulator. The inductor coil 46A emits RF waves establishing EMF wave fronts which are received by secondary inductor 48A. Further, transmitter electronic module 224 sends out command signals which are converted by modulator/demodulator decoder 220 and sent via antenna 222 to antenna 218 in the implanted stimulator. These received command signals are demodulated by decoder 216 and replied and responded to, based on a program in memory 214 (matched against a "command table" in the memory). Memory 214 then activates the proper controls and the inductor receiver coil 48A accepts the RF coupled power from inductor 46A.

The RF coupled power, which is alternating or AC in nature, is converted by the rectifier 508 into a high DC voltage. Small value capacitor 206 operates to filter and level this high DC voltage at a certain level. Voltage regulator 502 converts the high DC voltage to a lower precise DC voltage while capacitive power source 500 refreshes and replenishes.

When the voltage in capacative source 500 reaches a predetermined level (that is $V_{DD}$ reaches a certain predetermined high level), the high threshold comparator 230 fires and stimulating electronic module 212 sends an appropriate command signal to modulator/decoder 216. Modulator/decoder 216 then sends an appropriate "fully charged" signal indicating that capacitive power source 500 is fully charged, which is received by antenna 222 in the refresh-recharge transmitter unit 504.

In one mode of operation, the patient may start or stop stimulation by waving the magnet 242 once near the implant. The magnet emits a magnetic force $L_m$ which pulls reed switch 510 closed. Upon closure of reed switch 510, stimulating electronic module 212 in conjunction with memory 214 begins the delivery (or cessation as the case may be) of controlled electronic stimulation pulses to the sacral nerve 85 via electrodes 61, 62. In another mode (AUTO), the stimulation is automatically delivered to the implanted lead based upon programmed ON/OFF times.

The programmer unit 250 includes keyboard 232, programming circuit 238, rechargable battery 236, and display 234. The physician or medical technician programs programming unit 250 via keyboard 232. This program regarding the frequency, pulse width, modulation program, ON time etc. is stored in programming circuit 238. The programming unit 250 must be placed relatively close to the implanted stimulator 1 290 in order to transfer the commands and programming information from antenna 240 to antenna 218. Upon receipt of this programming data, modulator/demodulator and decoder 216 decodes and conditions these signals, and the digital programming information is captured by memory 214. This digital programming information is further processed by stimulating electronic module 212. In the DEMAND operating mode, after programming the implanted stimulator, the patient turns ON and OFF the implanted stimulator via hand held magnet 242 and a reed switch 510. In the automatic mode (AUTO), the implanted stimulator turns ON and OFF automatically according to the programmed values for the ON and OFF times.

Other simplified versions of such a system may also be used. For example, a system such as this, where a separate programmer is eliminated, and simplified programming is performed with a magnet and reed switch, can also be used.

The external stimulator (transmitter) may have a telecommunications module, as described in a co-pending application Ser. No. 09/837,565, and summarized here for reader convenience. The telecommunications module has two-way communications capabilities.

FIG. 20 shows conceptually, the data communication between the external stimulator 42 and a remote hand-held computer 558. A desktop or laptop computer 560 can be a server 500 which is situated remotely, perhaps at a physician's office or a hospital. The stimulation parameter data of the stimulator, can be viewed at this facility or reviewed remotely by medical personnel on a hand-held mobile device such as mobile digital assistant (MDA) 558, for example, a "palm-pilot" from PALM Corp. (Santa Clara, Calif.), a "HP Jornada" from Hewlitt Packard Corp. or on a personal computer (PC). The physician or appropriate medical personnel, is able to interrogate the external stimulator 42 device and know what the device is currently programmed to, as well as, get a graphical display of the pulse train. The wireless communication with the remote server 560 and hand-held mobile device 558 would be supported in all geographical locations within and outside the United States (US) that provides cell phone voice and data communication service. The pulse generation parameter data can also be viewed on the handheld devices (PDA) 558.

Figure 21:
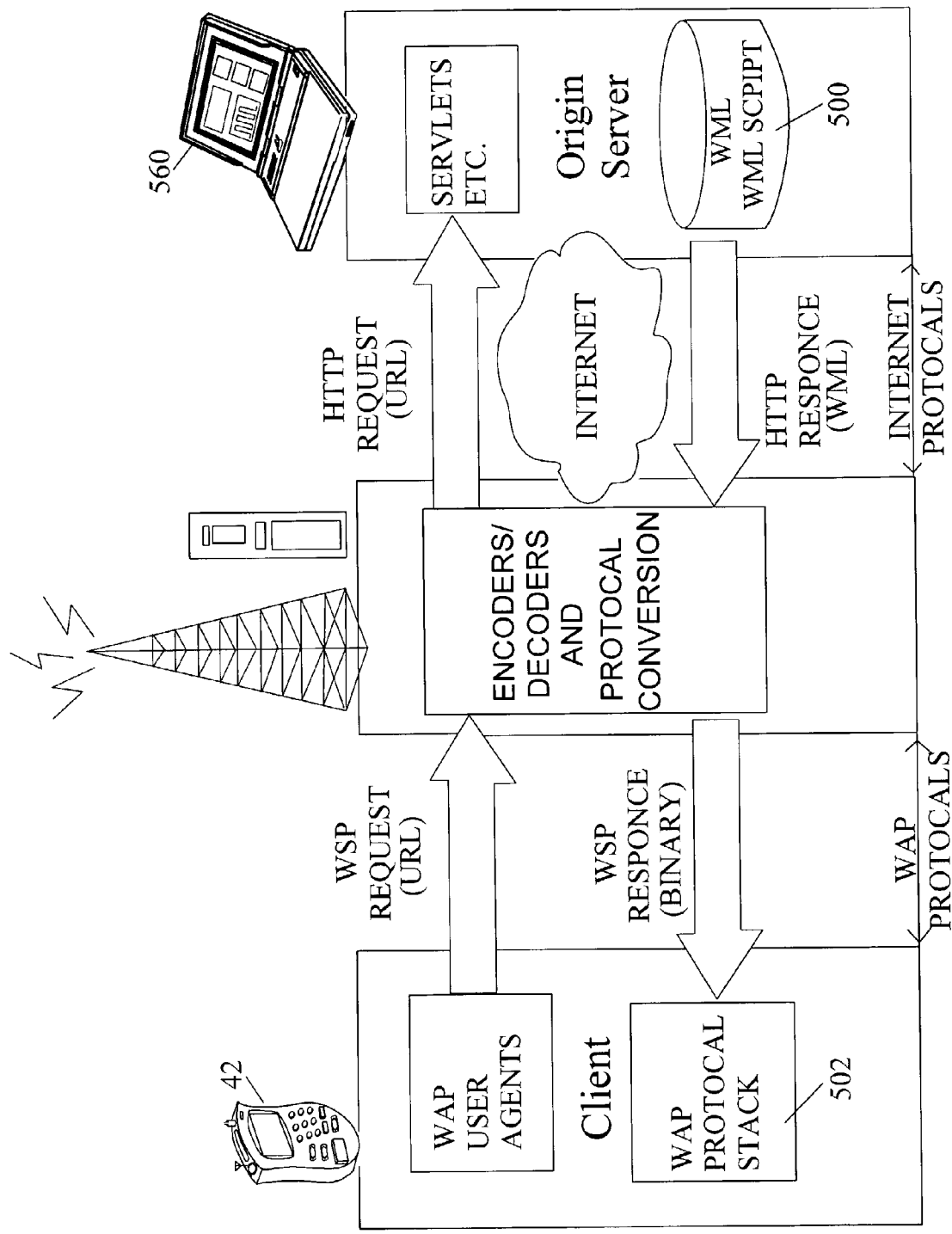
FIG. 21 is a schematic block diagram showing communication of stimulus generator over the wireless internet.

The telecommunications component of this invention uses Wireless Application Protocol (WAP). The Wireless Application Protocol (WAP) is a set of communication protocols standardizing Internet access for wireless devices. While previously, manufacturers used different technologies to get Internet on hand-held devices, with WAP devices and services interoperate. WAP promotes convergence of wireless data and the Internet. The WAP programming model is heavily based on the existing Internet programming model, and is shown schematically in FIG. 21. Introducing a gateway function provides a mechanism for optimizing and extending this model to match the characteristics of the wireless environment. Over-the-air traffic is minimized by binary encoding/decoding of Web pages and readapting the Internet Protocol stack to accommodate the unique characteristics of a wireless medium such as call drops. Such features are facilitated with WAP The key components of the WAP technology, as shown in FIG. 21, includes 1) Wireless Mark-up Language (WML) 500 which incorporates the concept of cards and decks, where a card is a single unit of interaction with the user. A service constitutes a number of cards collected in a deck. A card can be displayed on a small screen. WML supported Web pages reside on traditional Web servers. 2) WML Script which is a scripting language, enables application modules or applets to be dynamically transmitted to the client device and allows the user interaction with these applets. 3) Microbrowser, which is a lightweight application resident on the wireless terminal that controls the user interface and interprets the WML/WMLScript content. 4) A lightweight protocol stack 502 which minimizes bandwidth requirements, guaranteeing that a broad range of wireless networks can run WAP applications. The protocol stack of WAP can comprise a set of protocols for the transport (WTP), session (WSP), and security (WTLS) layers. WSP is binary encoded and able to support header caching, thereby economizing on bandwidth requirements. WSP also compensates for high latency by allowing requests and responses to be handled asynchronously, sending before receiving the response to an earlier request. For lost data segments, perhaps due to fading or lack of coverage, WTP only retransmits lost segments using selective retransmission, thereby compensating for a less stable connection in wireless. The above mentioned features are industry standards adopted for wireless applications and greater details have been publicized, and well known to those skilled in the art.

In this embodiment, two modes of communication are possible. In the first, the server initiates an upload of the actual parameters being applied to the patient, receives these from the stimulator, and stores these in its memory, accessible to the authorized user as a dedicated content driven web page. The physician or authorized user can make alterations to the actual parameters, as available on the server, and then initiate a communication session with the stimulator device to download these parameters.

The physician is also able to set up long-term schedules of stimulation therapy for their patient population, through wireless communication with the server. The server in turn communicates these programs to the neurostimulator 42. Each schedule is securely maintained on the server, and is editable by the physician and can get uploaded to the patient's stimulator device at a scheduled time. Thus, therapy can be customized for each individual patient. Each device issued to a patient has a unique identification key in order to guarantee secure communication between the wireless server 560 and stimulator device 42.

The second mode of communication is the ability to remotely interrogate and monitor the stimulation therapy on the physician's handheld (PDA) 458.

The present invention may be embodied in other specific forms without departing from the spirit or essential attributes thereof. It is therefore desired that the present embodiment be considered in all aspects as illustrative and not restrictive, reference being made to the appended claims rather than to the foregoing description to indicate the scope of the invention.

The invention claimed is:

1. A method of delivering electrical pulses to sacral nerves and/or its branches, comprising the steps of:
   providing an external pulse generator means for generating and transmitting modulated high frequency pulses, wherein said external pulse generator means comprises a primary coil, power supply, memory, circuitry to emit electrical pulses, and at least two predetermined programs to control said electrical pulses wherein at least one of the programs may be locked out to the patient;
   providing an implanted lead stimulus-receiver means for receiving, processing and delivering said pulses to said sacral nerves comprising electrical circuitry, replenishable or rechargeble power source, secondary coil, and at least one electrode adapted to be in contact with said sacral nerves and/or branches;
   activating one of said at least two predetermined programs of said external stimulator to emit said electrical pulses to said primary coil; and
   inductively transferring said electrical pulses from said primary coil of said external stimulator to said secondary coil of said lead stimulus receiver means;
   whereby, said electrical pulses are delivered to said sacral nerves and/or its branches.

2. The method of claim 1 wherein, said pulses are delivered for providing therapy or alleviating the symptoms for at least one of urinary incontinence and urological disorders.

3. The method of claim 1, wherein said electrical pulses have a carrier frequency ranging from 100 Kilo-Hertz to 100 Mega-Hertz.

4. The method of claim 1, wherein electrical pulse frequency delivered to said sacral nerves and/or branches ranges from 5 pulses per second to 500 pulses per second.

5. The method of claim 1, wherein pulse amplitude delivered to said sacral nerves and/or its branches range from 0.1 volts to 10 volts.

6. The method of claim 1, wherein pulse width of said electrical pulses delivered to said sacral nerves and/or its branches range from 20 micro-seconds to 5 milli-seconds.

7. The method of claim 1, wherein said electrical pulses are repeatedly applied to said nerves and/or its branches for applying therapy.

8. The method of claim 1, wherein variable parameters of said electrical pulses are adapted to be capable of being individually adjusted for the required therapy.

9. The method of claim 1, wherein variable parameters of said electrical pulses which are optimized for the patient are adapted to be stored in memory of said external pulse generator.

10. The method of claim 1, wherein said implanted lead stimulus receiver contains an internal power source comprising of replenishable capacative means.

11. The method of claim 1, wherein said implanted lead stimulus receiver contains a battery power source and memory device.

12. The method of claim 1, wherein said sacral nerves and/or its branches are stimulated by bipolar mode of stimulation.

13. The method of claim 1, wherein said sacral nerves and/or its branches are stimulated by unipolar mode of stimulation.

14. The method of claim 1, wherein said external pulse generator-transmitter comprises a telecommunications module.

15. The method of claim 1, wherein said external pulse generator means is adapted to be remotely programmed.

16. The method of claim 1, wherein said external pulse generator means is adapted to be remotely interrogated.

17. A method to selectively stimulate a sacral nerve and/or its branches, comprising the steps of:
   providing an external pulse generator-transmitter means comprising circuitry to emit electrical signals, memory, a power supply, at least two predetermined programs, a primary coil, and telecommunications module for remote communication;
   providing an implantable stimulus-receiving means comprising a secondary coil, circuitry, replenishable or rechargeable power source, and at least one electrode adapted to be in contact with said sacral nerve and/or its branches;
   activating one of said at least two predetermined programs of said external pulse generator-transmitter to emit said electrical signals to said primary coil; and
   inductively transferring said electrical signals from said external coil of said external generator to said secondary coil of said stimulus-receiver,
   whereby said electrical signals selectively stimulate said sacral nerve and/or its branches.

18. The method of claim 17, wherein said electrical signals emitted by said external pulse generator-transmitter range in frequency from 100 Kilo-Hertz to 100 Mega-Hertz.

19. The method of claim 17, wherein electrical stimulus pulse frequency delivered to said sacral nerve and/or its branches range from 5 pulses per second to 500 pulses per second.

20. The method of claim 17, wherein pulse amplitude delivered to said sacral nerve and/or its branches range from 0.1 volts to 10 volts.

21. The method of claim 17, wherein pulse width delivered to said sacral nerve and/or its branches range from 20 micro-seconds to 5 milli-seconds.

22. A system for providing therapy or alleviating the symptoms of urinary incontinence and urological disorders by providing electrical pulses to a sacral nerve(s) and/or its branches, comprising:
   an external pulse generator transmitter for generating and delivering modulated high frequency signals comprising circuitry, power source, primary coil, at least two predetermined programs wherein at least one of the programs is controlled by a patient;
   a lead stimulus-receiver adapted to be implanted for receiving, processing, and delivering said electrical pulses to said sacral nerves, comprising circuitry, secondary coil, replenishable or rechargeable power source, and at least one electrode adapted to be in contact with said sacral nerves and/or its branches; and
   said primary coil of said external pulse generator and said secondary coil of said implantable lead stimulus-receiver being capable of forming an electrical connection by inductive coupling,
   whereby, said electrical therapy is provided.

23. The system of claim 22, wherein said external pulse generator is adapted to provide signals rangeing in frequency from 100 Kilo-Hertz to 100 Mega-Hertz.

24. The system of claim 22, wherein electrical stimulus pulse frequency delivered to said sacral nerves and/or branches is adapted to range between 5 pulses per second to 500 pulses per second.

25. The system of claim 22, wherein pulse amplitude of the pulses delivered to the sacral nerves and/or branches is adapted to range between 0.1 volts to 10 volts.

26. The system of claim 22, wherein pulse width of electrical pulses of said external pulse generator transmitter is adapted to range between 20 micro-seconds to 5 milli-seconds.

27. The system of claim 22, wherein said signals from said external pulse generator transmitter are controlled by one of said at least two predetermined programs.

28. The system of claim 27, wherein at least one of said at least two predetermined programs is/are adapted to be locked out to the patient.

29. The system of claim 22, wherein variable parameters of said electrical pulses are adapted to be individually adjustable for the required therapy.

30. The system of claim 22, wherein said implanted lead stimulus receiver comprises an internal power source which consists of capacitor means.

31. The system of claim 22, wherein said implanted lead stimulus receiver comprises a battery power source and memory device.

32. The system of claim 22, wherein said external pulse generator transmitter further comprises a telecommunications module.

33. The system of claim 22, wherein said external pulse generator transmitter is adapted to be remotely programmable.

34. The system of claim 22, wherein said external pulse generator transmitter is adapted to be remotely interrogated.

* * * * *